(12) United States Patent  (10) Patent No.: US 7,981,882 B2
Briner et al.  (45) Date of Patent: Jul. 19, 2011

(54) 6-N-LINKED HETEROCYCLE-SUBSTITUTED 2,3,4,5-TETRAHYDRO-1H-BENZO[D] AZEPINES AS 5-HT$_{2C}$ RECEPTOR AGONISTS

(75) Inventors: Karin Briner, Indianapolis, IN (US); Anne Marie Camp, Basingstoke (GB); Alan Cornell, Basingstoke (GB); Michael Philip Mazanetz, Basingstoke (GB); Roger Ryan Rothhaar, Reelsville, IN (US); Frantz Victor, Indianapolis, IN (US); Andrew Caerwyn Williams, Basingstoke (GB); Deyi Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 652 days.

(21) Appl. No.: 11/995,212

(22) PCT Filed: Sep. 1, 2006

(86) PCT No.: PCT/US2006/034431
§ 371 (c)(1),
(2), (4) Date: Jan. 10, 2008

(87) PCT Pub. No.: WO2007/028132
PCT Pub. Date: Mar. 8, 2007

(65) Prior Publication Data
US 2008/0214520 A1  Sep. 4, 2008

Related U.S. Application Data

(60) Provisional application No. 60/713,504, filed on Sep. 1, 2005.

(51) Int. Cl.
*A61P 25/24*  (2006.01)
*A61K 31/55*  (2006.01)
*C07D 403/04*  (2006.01)
*C07D 405/14*  (2006.01)
*C07D 409/14*  (2006.01)
*C07D 223/16*  (2006.01)
*C07D 401/14*  (2006.01)

(52) U.S. Cl. .................. 514/217.01; 540/594
(58) Field of Classification Search ............. 514/217.01; 540/594
See application file for complete search history.

(56) References Cited

U.S. PATENT DOCUMENTS

| 4,265,890 | A | 5/1981 | Holden et al. |
| 4,985,352 | A | 1/1991 | Julius et al. |
| 5,639,748 | A | 6/1997 | DeMarinis et al. |
| 5,698,766 | A | 12/1997 | Julius et al. |

FOREIGN PATENT DOCUMENTS

| EP | 0285 287 | 10/1988 |
| EP | 1213017 A2 | 6/2002 |
| WO | WO 93/03015 | 2/1993 |
| WO | WO 93/04686 | 3/1993 |

(Continued)

OTHER PUBLICATIONS

Vikers et al., *Psycholpharmacology*, 167: 274-280 (2003).

(Continued)

*Primary Examiner* — Brenda Coleman
(74) *Attorney, Agent, or Firm* — R. Craig Tucker

(57) ABSTRACT

The present invention provides 6-substituted 2,3,4,5-tetrahydro-1H-benzo[d]azepines of Formula I as selective 5-HT$_{2C}$ receptor agonists for the treatment of 5-HT$_{2C}$ associated disorders including obesity, obsessive/compulsive disorder, depression, and anxiety: Formula (I) where: R$^6$ is selected from the group consisting of (a, b, c, d, e) and other substituents are as defined in the specification.

8 Claims, No Drawings

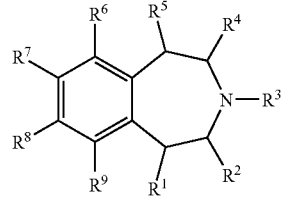

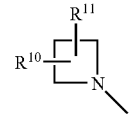

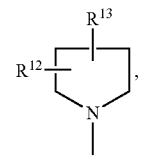

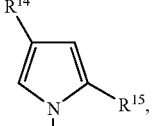

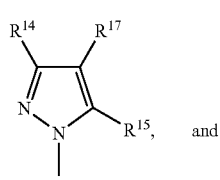

and

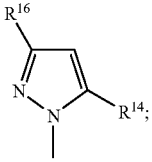

FOREIGN PATENT DOCUMENTS

| | | |
|---|---|---|
| WO | WO 93/04866 | 3/1993 |
| WO | WO 02/074746 | 9/2002 |
| WO | WO/02/074746 | 9/2002 |
| WO | WO 03 006466 | 1/2003 |
| WO | WO 03/045940 | 6/2003 |
| WO | WO 03/086306 | 10/2003 |
| WO | WO 2005/003096 | 1/2005 |
| WO | WO 2005/019179 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO 2006/069363 | 6/2006 |
| WO | WO 2006/071740 | 7/2006 |

OTHER PUBLICATIONS

Tecott et al., *Nature*, 374: 542-546 (1995).
Martin et al., *Pharmacol. Biochem. Behav.*, 71: 615 (2002).
Chou-Green et al., *Physiology & Behavior*, 78: 641-649 (2003).
Leysen et al., *Trends in Drug Research II*, 29: 49-61 (1998).
Frank et al., *Neuropsychopharmacology* 27: 869-873 (2002).
Upton et al., *Eur. J. Pharmacol.*, 359:33 (1998).
Fitzgerald, Ennis, *Annual Reports in Medicinal Chemistry*, 37: 21-30 (2002).
Nelson et al., *Naunyn-Schmiedeberg's Arch. Pharm.*, 359: 1-6 (1999).
V. Setola et al., *Mol. Pharmacology*, 63: 1223-1229 (2003).
Frishman, Kotob, *Journal of Clinical Pharmacology*, 39: 7-16 (1999).
Seeman, Van Tol, *Trends in Pharmacological Sciences*, 15: 264-270 (1994).
Data Base Registry: XP002419374, Sep. 30, 2008.
Database Registry: XP002419375, Sep. 30, 2008.
Database Registry: XP002419376, Sep. 30, 2008.
Database Registry: XP002419377, Sep. 30, 2008.

6-N-LINKED HETEROCYCLE-SUBSTITUTED 2,3,4,5-TETRAHYDRO-1H-BENZO[D]AZEPINES AS 5-HT$_{2C}$ RECEPTOR AGONISTS

This U.S. national stage application of International Application PCT/US2006/34431, filed Sep. 1, 2006, claims priority to U.S. provisional application Ser. No. 60/713,504, filed Sep. 1, 2005.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2A}$, 5-HT$_{2B}$, and 5-HT$_{2C}$. The 5-HT$_{2C}$ receptor has been isolated and characterized (Julius, et al., U.S. Pat. No. 4,985,352). Transgenic mice lacking the 5-HT$_{2C}$ receptor have been reported to exhibit seizures and an eating disorder resulting in increased consumption of food (Julius et al., U.S. Pat. No. 5,698,766). The 5-HT$_{2C}$ receptor has also been linked to various other neurological disorders including obesity (Vickers et al., Psychopharmacology, 167: 274-280 (2003)), hyperphagia (Tecott et al., Nature, 374: 542-546 (1995)), obsessive compulsive disorder (Martin et al., Pharmacol. Biochem. Behav., 71: 615 (2002); Chou-Green et al., Physiology & Behavior, 78: 641-649 (2003)), depression (Leysen, Kelder, Trends in Drug Research II, 29: 49-61 (1998)), anxiety (Curr. Opin. Invest. Drugs 2(4), p. 317 (1993)), substance abuse, sleep disorder (Frank et al., Neuropsychopharmacology 27: 869-873 (2002)), hot flashes (EP 1213017 A2), epilepsy (Upton et al., Eur. J. Pharmacol., 359: 33 (1998); Fitzgerald, Ennis, Annual Reports in Medicinal Chemistry, 37: 21-30 (2002)), and hypogonadism (Curr. Opin. Invest. Drugs 2(4), p. 317 (1993)).

Certain substituted 2,3,4,5-tetrahydro-1H-benzo[d]azepine compounds have been disclosed as useful therapeutics as for example:

U.S. Pat. No. 4,265,890 describes certain substituted 2,3,4,5-tetrahydro-1H-benzo[d]azepine compounds as dopaminergic receptor antagonists for use as antipsychotics and antiemetics, inter alia.

EP 0 285 287 describes certain substituted 2,3,4,5-tetrahydro-1H-benzo[d]azepine compounds for use as agents to treat gastrointestinal motility disorders, inter alia.

WO 93/03015 and WO 93/04686 describe certain substituted 2,3,4,5-tetrahydro-1H-benzo[d]azepine compounds as alpha-adrenergic receptor antagonists for use as agents to treat hypertension and cardiovascular diseases in which changes in vascular resistance are desirable, inter alia.

WO 02/074746 A1 describes certain substituted 2,3,4,5-tetrahydro-1H-benzo[d]azepine compounds as 5-HT$_{2C}$ agonists for the treatment of hypogonadism, obesity, hyperphagia, anxiety, depression, sleep disorder, inter alia.

WO 03/006466 A1 describes certain substituted tricyclic hexahydroazepinoindole and indoline compounds as 5-HT ligands and consequently their usefulness for treating diseases wherein modulation of 5-HT activity is desired.

WO 05/019180 describes 6-(2,2,2-trifluoroethylamino)-7-chloro-2,3,4,5-tetrahydro-1H-benzo[d]azepine as a potent and selective 5-HT$_{2C}$ agonist for the treatment of obesity, anxiety, depression, and obsessive-compulsive disorder.

High affinity 5-HT$_{2C}$ receptor agonists would provide useful therapeutics for the treatment of the above mentioned 5-HT$_{2C}$ receptor-associated disorders including obesity, hyperphagia, obsessive/compulsive disorder, depression, anxiety, substance abuse, sleep disorder, hot flashes, and hypogonadism. High affinity 5-HT$_{2C}$ receptor agonists that are also selective for the 5-HT$_{2C}$ receptor, would provide such therapeutic benefit without the undesirable adverse events associated with current therapies. Achieving selectivity for the 5-HT$_{2C}$ receptor, particularly as against the 5-HT$_{2A}$ and 5-HT$_{2B}$ receptors, has proven difficult in designing 5-HT$_{2C}$ agonists. 5-HT$_{2A}$ receptor agonists have been associated with problematic hallucinogenic adverse events. (Nelson et al., Naunyn-Schmiedeberg's Arch. Pharm., 359: 1-6 (1999)). 5-HT$_{2B}$ receptor agonists have been associated with cardiovascular related adverse events, such as valvulopathy. (V. Setola et al., Mol. Pharmacology, 63: 1223-1229 (2003), and ref. cited therein).

Previous references to substituted 2,3,4,5-tetrahydro-1H-benzo[d]azepine compounds as potential therapeutics have predominantly recited their uses as alpha adrenergic and/or dopaminergic modulators. Adrenergic modulators are often associated with the treatment of cardiovascular diseases (Frishman, Kotob, Journal of Clinical Pharmacology, 39: 7-16 (1999)). Dopaminergic receptors are primary targets in the treatment of schizophrenia and Parkinson's disease (Seeman, Van Tol, Trends in Pharmacological Sciences, 15: 264-270 (1994)). It will be appreciated by those skilled in the art that selectivity against these and other physiologically important receptors will generally also be preferred characteristics for therapeutics for the specific treatment of 5-HT$_{2C}$ associated disorders as described above.

The present invention provides potent and selective 5-HT$_{2C}$ agonist compounds of Formula I:

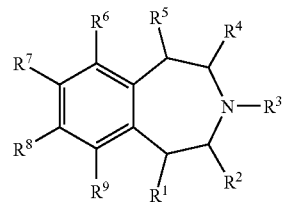

where:
$R^1$ is hydrogen, fluoro, or (C$_1$-C$_3$)alkyl;
$R^2$, $R^3$, and $R^4$ are each independently hydrogen, methyl, or ethyl;
$R^5$ is hydrogen, fluoro, methyl, or ethyl;
$R^6$ is selected from the group consisting of

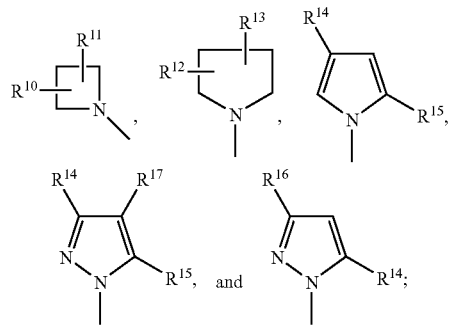

$R^7$ is hydrogen, halo, cyano, (C$_1$-C$_3$)alkyl optionally substituted with 1 to 5 fluoro substituents, (C$_2$-C$_6$)alkenyl optionally substituted with 1 to 6 fluoro substituents, (C$_3$-C$_7$)cycloalkyl, (C$_1$-C$_6$)alkoxy optionally substituted with 1 to 6 fluoro substituents, or (C$_1$-C$_6$)alkylthio optionally substituted with 1 to 6 fluoro substituents;
$R^8$ is hydrogen, halo, cyano, —SCF$_3$, or hydroxy;

$R^9$ is hydrogen, halo, cyano, —$CF_3$, —$SCF_3$, hydroxy, or $(C_1-C_3)$alkoxy optionally substituted with 1 to 6 fluoro substituents;

$R^{10}$ is hydrogen, 3-hydroxy, $(C_1-C_5)$alkyl optionally substituted with 1-6 fluoro groups, $Ph^1$-$(C_0-C_3)$alkyl, or $Ar^1$—$(C_0-C_3)$alkyl;

$R^{11}$ is hydrogen or $(C_1-C_3)$alkyl optionally substituted with 1-5 fluoro groups;

$R^{12}$ is hydrogen, $(C_1-C_5)$alkyl optionally substituted with 1-6 fluoro groups, $Ph^1$-$(C_0-C_3)$alkyl, or $Ar^1$—$(C_0-C_3)$alkyl;

$R^{13}$ is hydrogen or $(C_1-C_3)$alkyl optionally substituted with 1-5 fluoro groups;

$R^{14}$ is hydrogen, methyl or —$CF_3$;

$R^{15}$ is $(C_1-C_5)$alkyl, —$CF_3$, $Ph^1$, or $Ar^2$;

$R^{16}$ is $Ph^1$-$(C_1-C_3)$alkyl or $Ph^1$-S—$CH_2$—;

$R^{17}$ is hydrogen, halo, or methyl, provided that $R^{17}$ is hydrogen when $R^{15}$ is $Ph^1$ or $Ar^2$;

$Ph^1$ is phenyl optionally substituted with
  a) 1 to 5 fluoro substituents;
  b) 1 to 3 substituents independently selected from the group consisting of halo, cyano, methyl, hydroxy, and methoxy; or
  c) —$CF_3$ and optionally further substituted with 1 or 2 fluoro substituents;

$Ar^1$ is thienyl or pyridyl optionally substituted with
  a) 1 to 3 fluoro substituents; or
  b) 1 to 2 substituents independently selected from the group consisting of halo, cyano, and methyl;

$Ar^2$ is furyl, thienyl, or pyridyl optionally substituted with 1 to 2 substituents independently selected from the group consisting of halo, cyano, and methyl;

or a pharmaceutically acceptable salt or solvate thereof.

This invention also provides pharmaceutical compositions which comprise a compound of Formula I, or a pharmaceutically acceptable salt or solvate thereof, in association with a pharmaceutically acceptable carrier, diluent, or excipient.

In another aspect of the present invention, there is provided a method for treating a 5-$HT_{2C}$ receptor mediated disorder in mammals comprising administering to a mammal in need of such treatment an effective amount of a compound of Formula I, or a pharmaceutically acceptable salt or solvate thereof. Preferred 5-$HT_{2C}$ receptor mediated disorders include obesity, hyperphagia, obsessive compulsive disorder, depression, anxiety, substance abuse, sleep disorders, hot flashes, epilepsy and hypogonadism.

The present invention also provides a method for treating obesity in mammals comprising administering to a mammal in need of such treatment an effective amount of a compound of Formula I, or a pharmaceutically acceptable salt or solvate thereof.

The present invention also provides a method for treating obsessive/compulsive disorder in mammals comprising administering to a mammal in need of such treatment an effective amount of a compound of Formula I, or a pharmaceutically acceptable salt or solvate thereof.

Furthermore, the present invention provides a method for treating depression in mammals comprising administering to a mammal in need of such treatment an effective amount of a compound of Formula I, or a pharmaceutically acceptable salt or solvate thereof.

Furthermore, the present invention provides a method for treating anxiety in mammals comprising administering to a mammal in need of such treatment an effective amount of a compound of Formula I, or a pharmaceutically acceptable salt or solvate thereof.

In preferred embodiments of the above methods of treatment utilizing a compound of Formula I, or a pharmaceutically acceptable salt or solvate thereof, the mammal is a human.

In another aspect of the present invention, there is provided a compound of Formula I or a pharmaceutically acceptable salt or solvate thereof, for use in selectively increasing activation of the 5-$HT_{2C}$ receptor and/or for use in treating a variety of disorders associated with decreased activation of 5-$HT_{2C}$ receptors. Preferred embodiments of this aspect of the invention include a compound of Formula I for use in the treatment of obesity, hyperphagia, obsessive/compulsive disorder, depression, anxiety, substance abuse, sleep disorder, hot flashes, and/or hypogonadism. Particularly preferred embodiments of this aspect of the invention include the treatment of obesity, obsessive/compulsive disorder, depression, and/or anxiety.

In another aspect of the present invention, there is provided the use of one or more compounds of Formula I or pharmaceutically acceptable salts or solvates thereof, in the manufacture of a medicament for the activation of 5-$HT_{2C}$ receptors in a mammal. In preferred embodiments of this aspect of the invention, there is provided the use of one or more compounds of Formula I or pharmaceutically acceptable salts or solvates thereof, in the manufacture of a medicament for the treatment of obesity, hyperphagia, obsessive/compulsive disorder, depression, anxiety, substance abuse, sleep disorder, hot flashes, and/or hypogonadism. Particularly preferred embodiments of this aspect of the invention include the use of one or more compounds of Formula I or pharmaceutically acceptable salts or solvates thereof, in the manufacture of medicaments for the treatment of obesity, obsessive/compulsive disorder, depression, and/or anxiety.

Additionally, the present invention provides a pharmaceutical formulation adapted for the treatment of obesity, or for the treatment of obsessive/compulsive disorder, or for the treatment of depression, or for the treatment of anxiety, each of which comprise a compound of Formula I or a pharmaceutically acceptable salt or solvate thereof, in association with a pharmaceutically acceptable carrier, diluent or excipient.

In those instances where the disorders which can be treated by 5-$HT_{2C}$ agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The general chemical terms used throughout have their usual meanings. For example, the term "alkyl" refers to a branched or unbranched saturated hydrocarbon group. The term "n-alkyl" refers to an unbranched alkyl group. By way of illustration, but without limitation, the term "$(C_1-C_2)$alkyl" refers to methyl and ethyl. The term "$(C_1-C_3)$ n-alkyl" refers to methyl, ethyl, and propyl. The term "$(C_1-C_3)$alkyl" refers to methyl, ethyl, propyl, and isopropyl. The term "$(C_1-C_6)$ alkyl" refers to all branched and unbranched alkyl groups having from one to six carbon atoms.

$(C_x-C_y)$alkyl may also be used in conjunction with other substituents to indicate a branched or unbranched saturated hydrocarbon linker for the substituent, where x and y indicate the range of carbon atoms permitted in the linker moiety. By way of illustration, but without limitation, —$(C_0-C_2)$alkyl refers to a single bond, methylene, methyl-methylene, or ethylene linker moiety; —$(C_0-C_3)$alkyl further includes trimethylene, alpha- or beta-methyl ethylene, dimethyl methylene, or ethyl methylene. —$(C_1-C_3)$alkyl refers to a branched or unbranched alkylene linker having from 1 to 3 carbons.

The term "alkenyl" refers to a branched or unbranched unsaturated hydrocarbon group. By way of illustration, but without limitation, the term "$(C_2-C_6)$alkenyl" refers to a branched or unbranched hydrocarbon group having from 2 to 6 carbon atoms and 1 or more carbon-carbon double bonds.

The term "$(C_3-C_7)$cycloalkyl" refers to cyclopropyl, cyclobutyl, cyclopentyl, cyclohexyl and cycloheptyl.

The terms "alkoxy" and "sulfonyloxy" refer to an alkyl group or sulfonyl group, respectively, that is bonded through an oxygen atom.

The term "halo" refers to fluoro, chloro, bromo, or iodo. Preferred halo groups are fluoro, chloro, and bromo. More preferred halo groups are fluoro and chloro.

The term "amino protecting group" as used in this specification refers to a substituent commonly employed to block or protect the amino functionality while reacting other functional groups on the compound. Examples of such amino protecting groups include the formyl group, the trityl group, the acetyl group, the trichloroacetyl group, the trifluoroacetyl group, the chloroacetyl, bromoacetyl, and iodoacetyl groups, carbamoyl-type blocking groups such as benzyloxycarbonyl, 9-fluorenylmethoxycarbonyl ("FMOC"), t-butoxycarbonyl (t-BOC), and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of activating 5-$HT_{2C}$ receptors and/or elicit a given pharmacological effect.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. Known optical rotations are designated by (+) and (−) for dextrorotatory and levorotatory, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see for example, Berge, S. M, Bighley, L. D., and Monkhouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

Typical inorganic acids used to form such salts include hydrochloric, hydrobromic, hydroiodic, nitric, sulfuric, phosphoric, hypophosphoric, metaphosphoric, pyrophosphoric acid, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caproate, caprylate, cinnamate, citrate, formate, fumarate, glycolate, heptanoate, hippurate, lactate, malate, maleate, hydroxymaleate, malonate, mandelate, nicotinate, isonicotinate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate (mesylate), naphthalene-1-sulfonate, naphthalene-2-sulfonate, naphthalene-1,5-sulfonate, p-toluenesulfonate, xylenesulfonate, tartrate, and the like.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio. Terms such as "$(acid)_x$" are understood to mean that the molar ratio of the salt formed is not known and can not be presumed, as for example, but without limitation, $(HCl)_x$ and (methanesulfonic acid)$_x$.

Abbreviations used herein are defined as follows:
"Anal. Calc'd" means calculated elemental analysis.
"bp" means boiling point.
"BINAP" means rac-2,2'-bis(diphenylphosphino)-1,1'binaphthyl.
"Boc" or "t-Boc" means tert-butoxycarbonyl.
"Brine" means a saturated aqueous sodium chloride solution.

"CV" means calorific value of oxygen.
"DCM" means dichloromethane (i.e. methylene chloride, $CH_2Cl_2$).
"DMF" means N,N-dimethylformamide.
"DMSO" means dimethylsulfoxide.
"EE" means energy expenditure.
"EtOAc" means ethyl acetate.
"GC-MS" means gas chromatography-mass spectrometry.
"GDP" means guanosine diphosphate.
"GTP" means guanosine triphosphate.
"GTPγ[$^{35}$S]" means guanosine triphosphate having the terminal phosphate substituted with $^{35}$S in place of an oxygen.
"HMPA" means hexamethylphosphoramide.
"HPLC" means high-pressure liquid chromatography.
"ISPA" means immunoadsorption scintillation proximity assay.
"mp" means melting point.
"MS (ES+)" means mass spectroscopy using electrospray ionization.
"MTBE" means methyl t-butyl ether.
"NMP" means 1-methyl-2-pyrrolidinone.
"NMR" means nuclear magnetic resonance.
"Pd/C" means palladium on activated carbon.
"RQ" means respiratory quotient.
"RT" means room temperature.
"SCX chromatography" means chromatography on an SCX column or cartridge.
"SCX column" or "SCX cartridge", as used herein, refers to a Varian Bond Elute® silica based strong cation exchange resin column or disposable cartridge or equivalent.
"TFA" means trifluoroacetic acid.
"THF" means tetrahydrofuran.
"TLC" means thin layer chromatography.

While all of the compounds of the present invention are useful as $5\text{-HT}_{2C}$ agonists, certain classes are preferred, as for example, compounds having any of the following enumerated selections of substituents: Compounds wherein 1) $R^7$ is halo;
2) $R^7$ is chloro;
3) $R^7$ is fluoro;
4) $R^7$ is $(C_1\text{-}C_6)$alkyl optionally substituted with 1 to 6 fluoro substituents;
5) $R^7$ is $(C_1\text{-}C_3)$alkyl optionally substituted with 1 to 6 fluoro substituents;
6) $R^7$ is ethyl;
7) $R^7$ is —$CF_3$;
8) $R^7$ is $(C_3\text{-}C_6)$alkenyl optionally substituted with 1 to 6 fluoro substituents;
9) $R^7$ is $(C_3\text{-}C_6)$alkenyl;
10) $R^7$ is cyano;
11) $R^{1\text{-}5}$ are each hydrogen;
12) $R^5$ is methyl or ethyl;
13) $R^5$ is methyl;
14) $R^3$ is methyl;
15) $R^5$ is hydrogen;
16) $R^9$ is hydrogen;
17) $R^9$ is $(C_1\text{-}C_3)$alkoxy optionally substituted with 1 to 5 fluoro substituents;
18) $R^9$ is methoxy;
19) $R^9$ is halo;
20) $R^9$ is chloro;
21) $R^9$ is cyano;
22) $R^9$ is —$CF_3$;

23) $R^6$ is

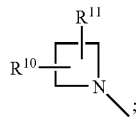

24) $R^6$ is

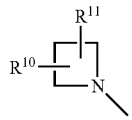

and $R^{10}$ and $R^{11}$ are each hydrogen;

25) $R^6$ is

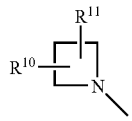

and $R^{10}$ and $R^{11}$ are each methyl;

26) $R^6$ is

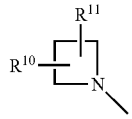

and $R^{10}$ is $Ph^1\text{-}(C_0\text{-}C_3)$alkyl;

27) $R^6$ is

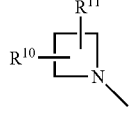

and $R^{10}$ is $Ph^1$- (i.e. $C_0$-alkyl);

28) $R^6$ is

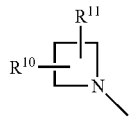

and $R^{10}$ is $Ph^1$- and is adjacent to the azetidinyl nitrogen;

29) $R^6$ is any one of embodiments 26) through 28) and $Ph^1$ is mono-substituted;

30) $R^6$ is

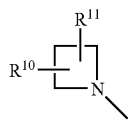

and $R^{10}$ is $Ar^1$—$(C_0$-$C_3)$alkyl;

31) $R^6$ is

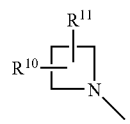

and $R^{10}$ is $Ar^1$—;

32) $R^6$ is

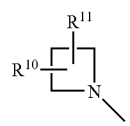

and $R^{10}$ is $Ar^1$— and is adjacent to the azetidinyl nitrogen;

33) $R^6$ is any one of embodiments 30) through 32) and $Ar^1$ is mono-substituted;

34) $R^6$ is any one of embodiments 30) through 32) and $Ar^1$ is unsubstituted;

35) Any one of embodiments 26) through 34) where $R^{11}$ is hydrogen;

36) $R^6$ is

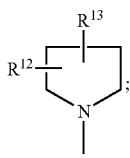

37) $R^6$ is

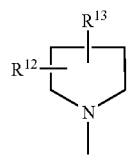

and $R^{12}$ is $C_{1-3}$ alkyl;

38) $R^6$ is

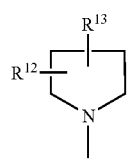

and $R^{12}$ is methyl;

39) $R^6$ is

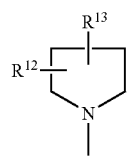

and $R^{12}$ is 2-methyl;

40) $R^6$ is

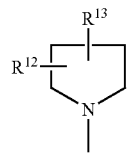

and $R^{12}$ is $Ph^1$-$(C_0$-$C_3)$alkyl;

41) $R^6$ is

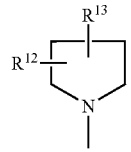

and $R^{12}$ is $Ph^1$- (i.e. $C_0$-alkyl);

42) $R^6$ is

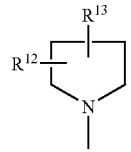

and $R^{12}$ is $Ph^1$- and is at the 2-position of the pyrrolidinyl ring;

43) $R^6$ is any one of embodiments 40) through 42) and $Ph^1$ is mono-substituted;

44) $R^6$ is and $R^{12}$ is $Ar^1$—$(C_0$-$C_3)$alkyl;

45) $R^6$ is

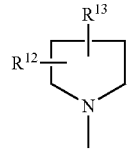

and $R^{12}$ is $Ar^1$— (i.e. $C_0$-alkyl);

46) $R^6$ is

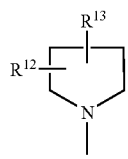

and $R^{12}$ is $Ar^1$— and is at the 2-position of the pyrrolidinyl ring;

47) $R^6$ is any one of embodiments 44) through 46) and $Ar^1$ is mono-substituted;

48) $R^6$ is any one of embodiments 44) through 46) and $Ar^1$ is unsubstituted;

49) Any one of embodiments 37-48 where $R^{13}$ is hydrogen;

50) $R^6$ is

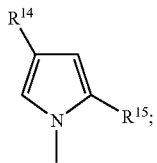

51) $R^6$ is

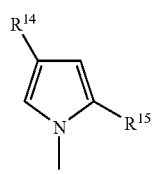

where $R^{14}$ is hydrogen;

52) $R^6$ is

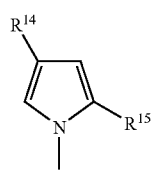

where $R^{15}$ is mono-substituted;

53) $R^6$ is

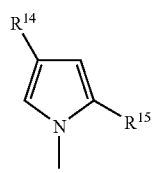

where $R^{15}$ is mono-substituted and $R^{14}$ is methyl;

54) $R^6$ is

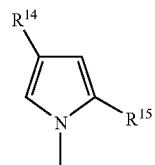

where $R^{15}$ is mono-substituted and $R^{14}$ is hydrogen;

55) $R^6$ is

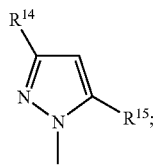

56) $R^6$ is

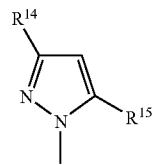

where $R^{14}$ is hydrogen or methyl and $R^{15}$ is $(C_1\text{-}C_5)$alkyl, $Ph^1$, or $Ar^2$;

57) $R^6$ is

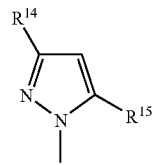

where $R^{15}$ is $(C_1\text{-}C_5)$alkyl;

58) $R^6$ is

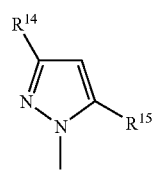

where $R^{15}$ is methyl;

59) $R^6$ is

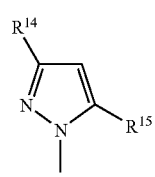

where $R^{15}$ is $Ph^1$;

60) $R^6$ is

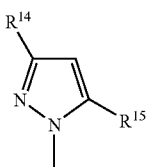

where $R^{15}$ is mono-substituted $Ph^1$;
61) $R^6$ is

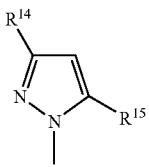

where $R^{15}$ is $Ar^2$;
62) $R^6$ is

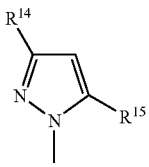

where $R^{15}$ mono-substituted $Ar^2$;
63) $R^6$ is

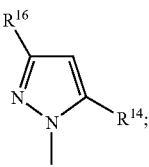

64) $R^6$ is

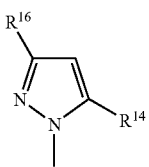

and $R^{16}$ is $Ph^1$-$(C_1$-$C_3)$alkyl;
65) $R^6$ is

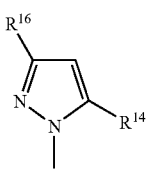

and $R^{16}$ is $Ph^1$-S—$CH_2$—;
66) Any one of embodiments 55-65 where $R^{14}$ is hydrogen;
67) Any one of embodiments 55-65 where $R^{14}$ is at methyl; and
68) $R^7$ is chloro and $R^{1-5,8,9}$ are each hydrogen.

It will be understood that the above classes may be combined to form additional preferred classes. Exemplary combinations include, but are not limited to:

69) Any one of preferred embodiments 1) through 10) (the preferred selections for $R^7$), combined with any one of preferred embodiments 11) through 22) (the preferred selections for $R^{1-5,8,9}$);

70) Any one of preferred embodiments 23) through 35) (the preferred selections for $R^6$ being azetidinyl), combined with any one of preferred combinations described in 69);

71) Any one of preferred embodiments 36) through 49) (the preferred selections for $R^6$ being pyrrolidinyl), combined with any one of preferred combinations described in 69);

72) Any one of preferred embodiments 50) through 54) (the preferred selections for $R^6$ being pyrrolyl), combined with any one of preferred combinations described in 69);

73) Any one of preferred embodiments 55) through 67) (the preferred selections for $R^6$ being pyrazolyl), combined with any one of preferred combinations described in 69);

74) Any one of preferred combinations 70) through 73) wherein $R^7$ is chloro; and 75) Any one of preferred combinations 70) through 73) wherein $R^7$ is chloro and $R^{1-5,8,9}$ are each hydrogen.

Also, in general, when $R^{10,12,15,\ or\ 16}$ is substituted $Ph^1$, mono substitution in the phenyl 3- or 4-position is preferred, with substitution in the 4-position generally being the more preferred.

The compounds of the invention can be prepared according to the following synthetic schemes by methods well known and appreciated in the art, by methods described herein, and by analogy to such methods. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired including, but not limited to, extraction, evaporation, precipitation, chromatography, filtration, trituration, crystallization and the like. Frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties as is well appreciated by those of ordinary skill in the art. In addition, the skilled artisan will appreciate that intermediates of Formula I or final products of Formula I may result in the formation of isomers which may be separated by techniques well-known in the art. In an optional step, an acid addition salt may be formed using a pharmaceutically acceptable acid. The formation of acid addition salts is well known and appreciated in the art.

Compounds of Formula I may be prepared as illustrated in the following schemes. All substituents, unless otherwise indicated, are as previously defined, and all reagents are well known and appreciated in the art. Pg is a suitable protecting group for a secondary amine such as, but not limited to, 2,2,2-trifluoroacetyl or tert-butoxycarbonyl. The selection and use of suitable protecting groups is well known and appreciated in the art (see for example, *Protecting Groups in Organic Synthesis*, Theodora Greene (Wiley-Interscience)).

Generally, the compounds according to Formula I may be synthesized by derivatizing the appropriately substituted and N-protected 6-hydroxy-1,2,3,4-tetrahydrobenzazepine intermediate. Schemes 1 and 2 illustrate two methods to obtain these intermediates, though the skilled artisan will appreciate that alternative methods may also be available.

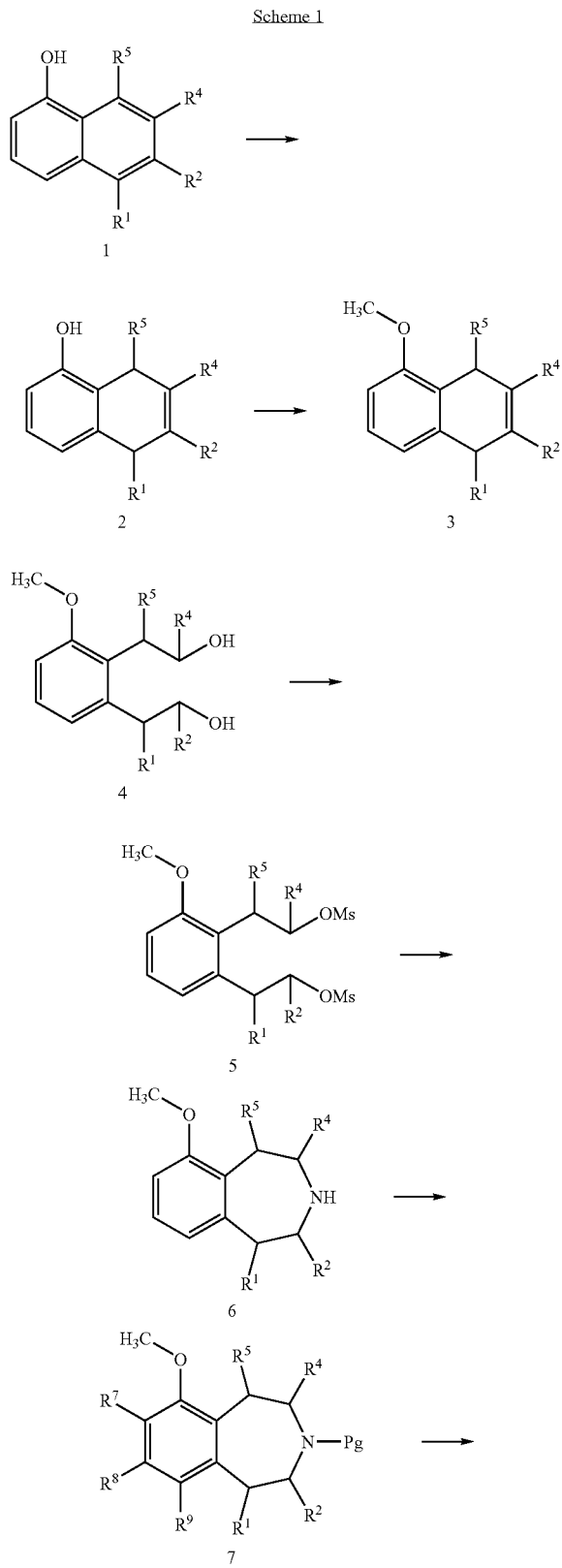

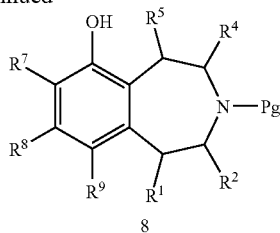

Optionally substituted 1-naphthol 1 is converted to the corresponding 5-hydroxy-1,4-dihydronaphthalene compound 2 by a Birch reduction using ammonia and lithium metal at low temperature. Methylation of the 6-hydroxy group using well known conditions affords the methoxy analog 3. Treatment with ozone at −65° C. in a suitable solvent, followed by the addition of a reducing agent, such as sodium borohydride, at 0° C. reduces the ozonide to the diol 4. The diol 4 is then derivatised to provide two leaving groups, such as methanesulfonates, to give compound 5 or the like. Cyclization to the corresponding 6-methoxy-3-Pg-2,3,4,5-tetrahydro-1H-benzo[d]azepine 6 may be accomplished by heating 5 in a closed reaction vessel in a suitable solvent containing concentrated ammonium hydroxide. Protection of the ring nitrogen with any of a variety of alkyl halides, acid chlorides, or anhydrides such as trifluoroacetic anhydride or tert-butoxycarbonyl gives compound 7. Removal of the methyl ether and addition of 1 M boron tribromide in a suitable solvent like DCM at 0° C. provides the desired N-protected, 6-hydroxy-2,3,4,5-tetrahydro-1H-benzo[d]azepine intermediate 8.

Functionalization of the aromatic ring to introduce substituents $R^7$, $R^5$ and/or $R^9$ as desired are well known in the art and vary depending on the substitution desired.

Alternatively, compound 12 can be prepared from 1,2-bis(cyanomethyl)-3-methoxybenzene 9, as shown in Scheme 2, as previously described in the literature (J. Med. Chem., 1984, 27, 918-921).

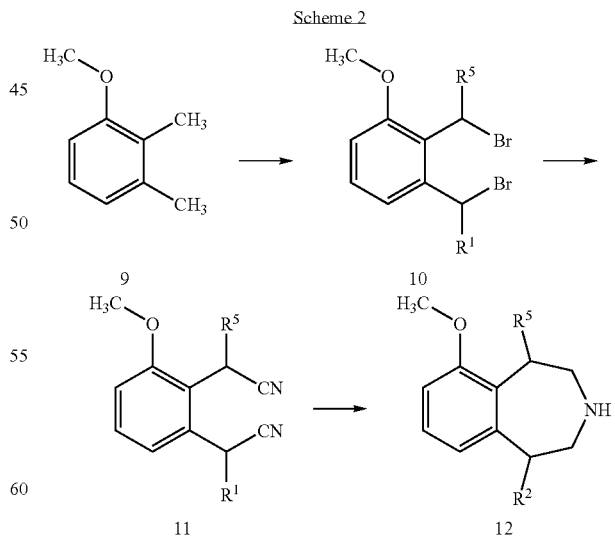

Compounds wherein $R^6$ is optionally substituted pyrazolyl can be made by converting the 6-hydroxy group to the triflate analog, reacting the triflate with benzophenone hydrazone using sodium tert-butoxide, BINAP and bis(dibenzylidineacetone)palladium (0) to give the N-benzhydrylidene-hydrazine analog, and then reacting the intermediate with an appropriately substituted dione in a cyclization reaction followed by deprotection. (Scheme 3)

analog 13. The triflate is displaced with benzophenone hydrazone using sodium tert-butoxide, BINAP and bis(dibenzylidineacetone)palladium (0) to give the N-benzhydrylidene-hydrazine analog 14. Ring formation by reaction of 14 with a substituted or unsubstituted 2,4-pentanedione in a suitable solvent with 10 N HCl gives the corresponding pyrazole compound 15. Removal of the protecting group provides pyrazole compounds of Formula II.

Compounds wherein $R^6$ is optionally substituted pyrrolyl can be made by converting the 6-hydroxy group to an amine and then reacting with an appropriately substituted butanone in a cyclization reaction followed by deprotection. (Scheme 4)

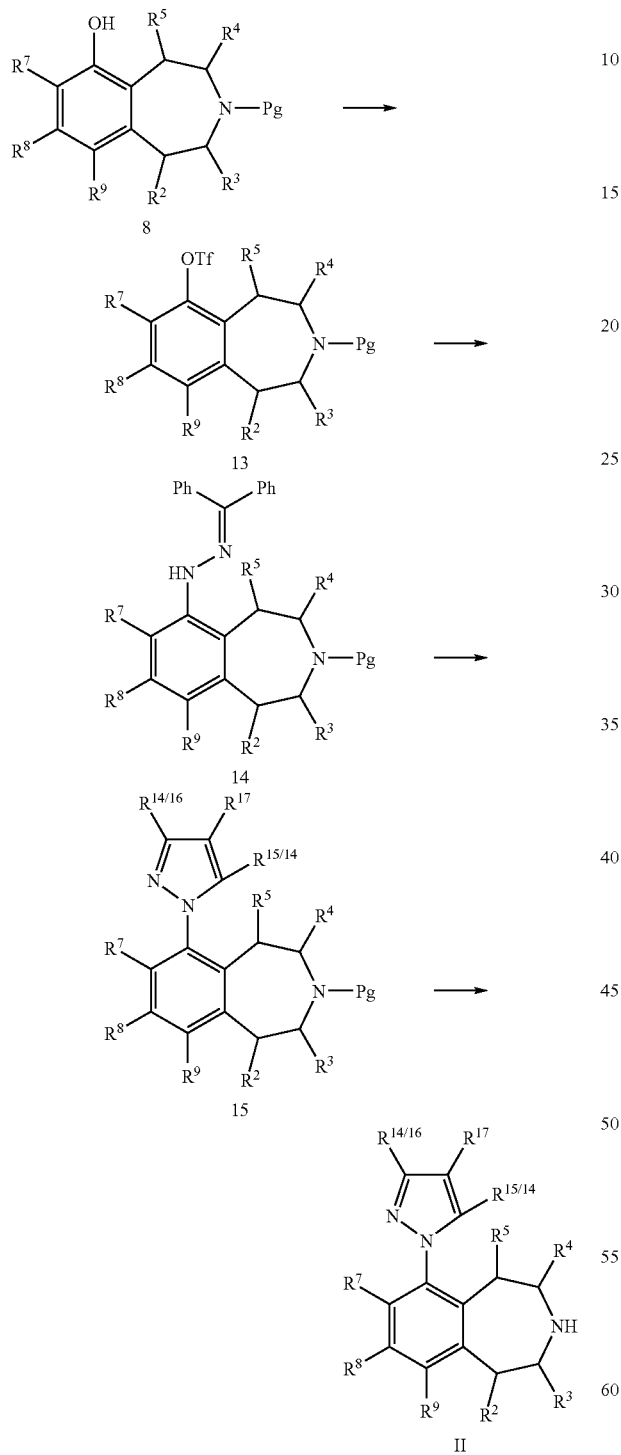

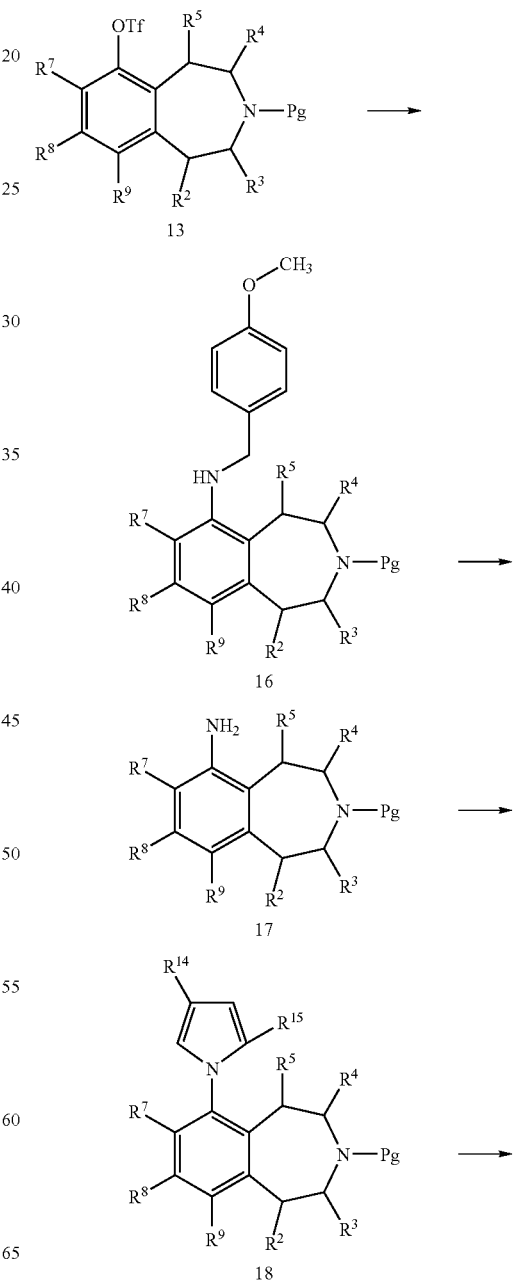

Generally, the 6-hydroxy intermediate 8, is treated with trifluoromethanesulfonic anhydride, with triethylamine in DCM using standard known chemistry to give the triflate -continued

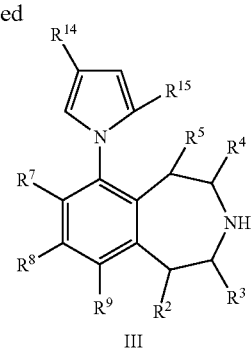

III

Generally, the appropriate triflate 13, is converted to the corresponding amine 17 by reaction with 4-methoxybenzylamine using tris(dibenzylideneacetone)-dipalladium (0), BINAP and cesium carbonate to give a secondary amine 16, which is then treated with 3-dichloro-5,6-dicyano-1,4-benzoquinone. This amine 17 is then refluxed with an appropriately substituted 3-(1,3-dioxan-2-yl)propiophenone with p-toluene sulfonic acid to cyclize the pyrrolyl ring in compound 18. The protecting group is removed to give compounds of Formula III. Alternatively, 17 may be reacted with 2,5-dimethoxytetrahydrofuran in refluxing glacial acetic acid to give compound 18.

Compounds wherein $R^6$ is optionally substituted azetidinyl can be made by converting the 6-hydroxy group to an amine as described above, and then reacting an amine 17 with an appropriately substituted butanone in a cyclization reaction followed by deprotection. (Scheme 5)

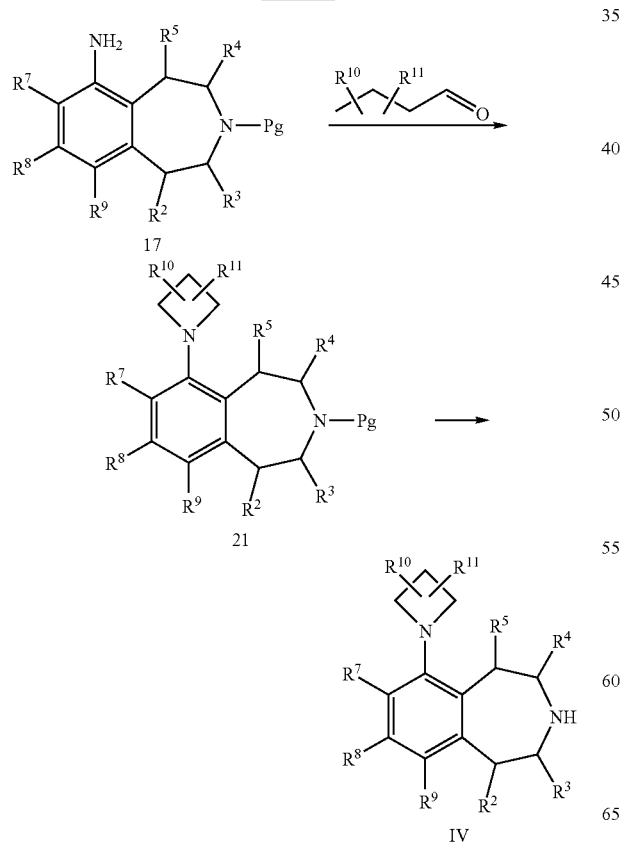

Alternately, compound 13, prepared as previously described, is reacted with optionally substituted azetidine using palladium acetate, BINAP, and cesium carbonate under typical Buchwald conditions to give compound 21. The protecting group is cleaved to give a compound of Formula IV.

Scheme 6

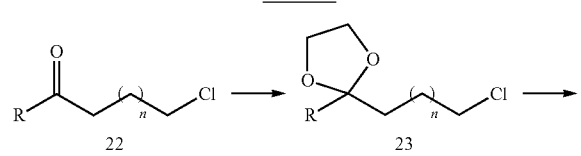

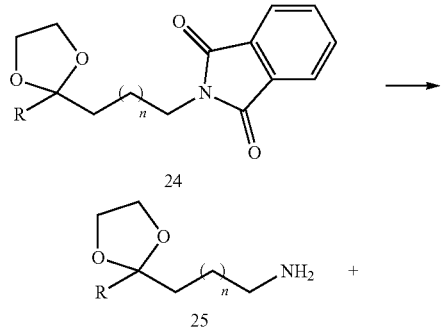

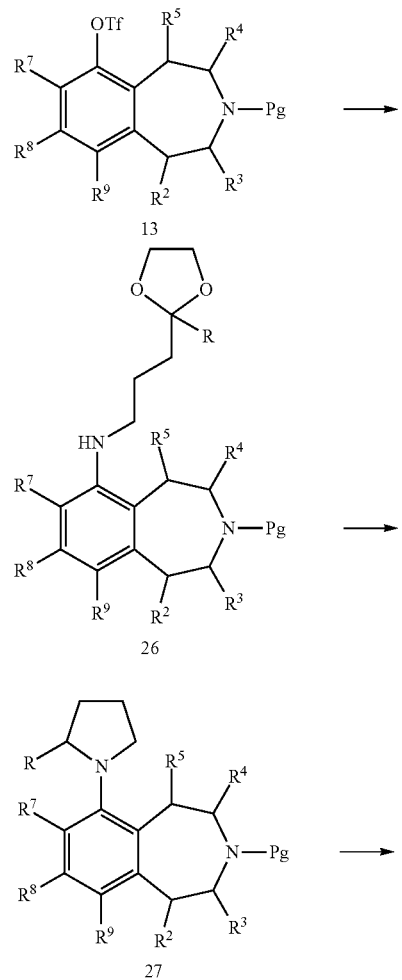

-continued

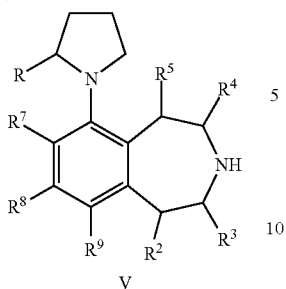

Compound 22, where R is substituted or unsubstituted aryl or alkyl groups and X is a leaving group, such as halide, is treated with ethylene glycol with p-toluene sulfonic acid in refluxing benzene to give the [1,3]dioxolane analog 23, which is then treated with potassium phthalimide to give compound 24. Compound 24 is treated with 2 M methylamine to give the primary amine compound 25. Using typical Buchwald conditions, 25 is reacted with compound 13, prepared as previously described, to give the secondary amine compound 26. Cyclization of 26 with acid, such as 2 N hydrochloric acid, followed by treatment with a base like cyanoborohydride gives compound 27. The protecting group is cleaved to give a compound of Formula V.

Alternatively, an appropriately substituted pyrrolidine may be reacted directly with compound 13 using typical Buchwald conditions to provide pyrrolidinyl compounds having the desired substitutions on the pyrrolidinyl ring.

The following Preparations and Examples are illustrative of methods useful for the synthesis of the compounds of the present invention. Exemplified compounds are also particularly preferred compounds of the present invention.

Preparation 1

7-Chloro-3-(2,2,2-trifluoroacetyl)-6-trifluoromethanesulfonyloxy-2,3,4,5-tetrahydro-1H-benzo[d]azepine

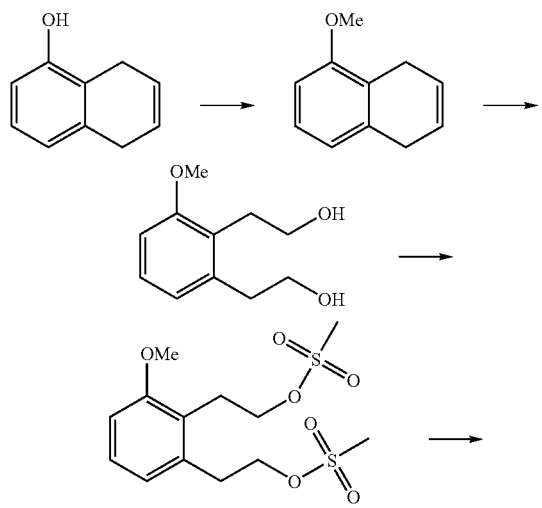

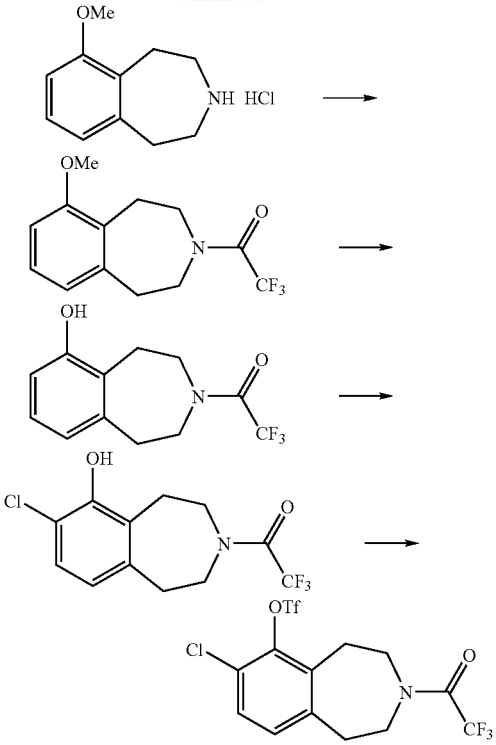

5-Methoxy-1,4-dihydronaphthalene

Add powdered potassium carbonate (193.1 g, 1.397 mol) to a solution of commercially available 5,8-dihydronaphthalen-1-ol [68.08 g, 90% potency based on $^1$H-NMR, 0.4657 mol, from Societa Italiana Medicinala Scandicci, s.r.l., Reggello (Firenze), Italy] in ethanol (700 mL). Cool the solution to 0° C. with ice water and add dimethyl sulfate (88.1 g, 66.1 mL, 0.699 mol) dropwise, maintaining the temperature between 5° C. and 10° C. Heat the reaction mixture to 40° C. until TLC shows the absence of starting material (about 2 hr). Filter off the solids by vacuum filtration and concentrate. Dilute the residual brown oil with diethyl ether (500 mL), wash with 10% aqueous ammonium hydroxide (500 mL), water (500 mL), brine (500 mL), dry (sodium sulfate) and concentrate to give the crude product as a brown oil (73 g). Purify the crude product by short path distillation under vacuum (bp 120-130° C./5 Torr) to give the title compound as a clear oil (69.0 g, 92.5% potency corrected) (contains some 1,2,3,4-tetrahydro-5-methoxynaphthalene as an impurity).

$^1$H NMR (300 MHz, CDCl$_3$), δ 7.15 (t, 1H, J=7.9), 6.72 (dd, 2H, J=15.7, 7.9), 5.93-5.88 (m, 2H), 3.83 (s, 3H), 3.42-3.39 (m, 2H), 3.30-3.28 (m, 2H)

2,3-Bis-(2-hydroxyethyl)-1-methoxybenzene

Charge a four-neck 5 L flask equipped with an over-head mechanical stirrer, reflux condenser, thermocouple, and gas dispersion apparatus with 5-methoxy-1,4-dihydronaphthalene (264.54 g, 89.5% potency based on $^1$H-NMR, 1.478 mol) in DCM (1.3 L) and ethanol (1 L). Add sudan III (10 mg) to give a faint red color. Cool the solution to −65° C. or lower, then pass 03 through the solution until the solution turns a light yellow color and the TLC shows the absence of the starting material (about 30 hr). Transfer the solution via cannula into a slurry of sodium borohydride (97.8 g, 2.59 mol) in ethanol (500 mL) cool in an ice water and maintain the temperature at or above 0° C., as for example between 0° C. and 10° C., throughout the transfer to ensure the ozonide is completely reduced to the diol. After the transfer is complete, warm the solution to RT and stir for about 30 min. Cool the slurry to 0° C. with ice water then slowly add acetone (540 mL, 7.4 mol) to remove excess sodium borohydride. After all the solids dissolve, concentrate and redissolve the yellow solid in DCM (1 L) and water (1 L), separate the layers and extract the aqueous layer with DCM (750 mL). Wash the combined organic layers with brine (1.5 L), add toluene (750 mL) and concentrate. Dissolve the solid in DCM (500 mL) with heating, then add toluene (750 mL) and concentrate to give the title compound as a light yellow solid (283.7 g, 89% potency corrected, mp 82-83° C.) (contains 1,2,3,4-tetrahydro-5-methoxynaphthalene as an impurity (8.6%)). Further purify the product by vacuum drying overnight at 75° C., 5 Torr, to remove all but trace amount of the 1,2,3,4-tetrahydro-5-methoxynaphthalene impurity. $^1$H NMR (300 MHz, CDCl$_3$), δ 7.16 (dd, 1H, J=8.2, 7.6), 6.83 (s, 1H, J=7.0), 6.76 (s, 1H, J=8.2), 3.85-3.77 (m, 7H), 3.01-2.91 (m, 4H), 2.35 (s, 2H); $^{13}$C NMR (300 MHz, DMSO-d6), δ 157.5, 138.9, 126.5, 125.2, 122.0, 108.4, 62.1, 60.5, 55.3, 36.1, 29.6; IR (KBr): 3006, 2960, 2886, 2829, 1583, 1461, 1440, 1264, 1091, 1041 cm$^{-1}$; MS (ES): m/z=178 [M+H]; Anal. Calc'd for C$_{11}$H$_{16}$O$_3$: C, 67.32; H, 8.22; N, O. Found: C, 67.26, H, 8.10; N, 0.21.

2,3-Bis-(2-methanesulfonyloxyethyl)-1-methoxybenzene

To a slurry of 2,3-bis-(2-hydroxyethyl)-1-methoxybenzene (50.6 g, 0.258 mol, 1 equiv.) and triethylamine (78.3 g, 0.774 mol, 3 equiv.) in DCM (500 mL) at 0° C., add dropwise a solution of methanesulfonyl chloride (65.0 g, 0.567 mol, 2.2 equiv.) in DCM (100 mL) over 45 min. The addition is exothermic and the methanesulfonyl chloride is added at a rate to keep the temperature below 10° C. After the addition is complete, warm the reaction to RT. Wash the solution with water (2×500 mL), and then brine (750 mL). Dry (sodium sulfate) and concentrate to give the title compound as a dark yellow oil (87.4 g, 96.2%), which is used in the next reaction without further purification. An analytical sample is obtained utilizing silica gel chromatography, eluting with 100% diethyl ether.
$^1$H NMR (300 MHz, CDCl$_3$), δ 7.20 (t, 1H, J=7.9), 6.82 (s, 1H, J=7.2), 6.80 (s, 1H, J=8.2), 4.41-4.34 (m, 4H), 3.83 (s, 3H), 3.16-3.09 (m, 4H), 2.91 (s, 3H), 2.87 (s, 3H); $^{13}$C NMR (300 MHz, CDCl$_3$), δ 158.07, 136.55, 128.26, 123.34, 122.39, 109.24, 69.88, 69.08, 55.55, 37.35, 37.14, 32.57, 26.47; $^{13}$C NMR (300 MHz, DMSO-d6), δ 157.58, 136.79, 127.81, 122.91, 122.00, 109.33, 70.19, 68.88, 55.55, 36.49, 36.47, 31.56, 25.72; IR (KBr): 1586.8, 1469.4, 1358.51, 1267.3, 1173.9, 1105.4, 972.4, 954.6, 914.3 cm$^{-1}$; MS (ES): m/z=257 [M+H]; Anal. Calc'd. for C$_{13}$H$_{20}$O$_7$S$_2$: C, 44.31; H, 5.72; N, O. Found: C, 44.22, H, 5.68; N, 0.13.

6-Methoxy-2,3,4,5-tetrahydro-1H-benzo[d]azepine

Dissolve 2,3-bis-(2-methanesulfonyloxyethyl)-1-methoxybenzene (474.4 g, 1.346 mol) in acetonitrile (7 L) and split the mixture into two equal lots. In two separate runs, add concentrated ammonium hydroxide (3.5 L) and charge the solution into a pressure vessel (PARR apparatus). Heat the solution in a closed reactor to 100° C. over 20 min (internal pressure reaches about 100 psi), and maintain at 100° C. until the reaction is complete (about 1 h, HPLC monitored). Cool the reaction mixture to RT. Combine the two lots and concentrate. Dissolve the residue in MTBE (3.5 L) and water (3.5 L). Adjust the pH to 6.5 using 2 N NaOH or 1 N HCl as appropriate (typically the pH is about pH=5.1 and the adjustment requires about 50 mL 2 N NaOH). Discard the organic layer, adjust the aqueous layer to pH=13 using 50% NaOH (~150 mL). Extract with MTBE (2×3.5 L), wash the combined organic layers with brine (3.5 L), dry (sodium sulfate) and concentrate to give the title compound as a crude yellow oil that solidifies upon standing (179.3 g). Use the material for the next step without further purification. Prepare an analytical sample by purification by two Kugelrohr distillations to give a clear oil that solidifies upon standing.
$^{13}$C NMR (300 MHz, DMSO-d6) δ 156.1, 144.4, 130.3, 126.2, 121.5, 108.9, 55.5, 48.2, 47.9, 39.9, 29.1; mp 44.3-45.0° C.; MS (ES): m/z=163 [M+H]; Anal. Calc'd for C$_{11}$H$_{15}$NO: C, 74.54; H, 8.53; N, 7.90. Found: C, 74.28, H, 8.62; N, 7.86.

6-Methoxy-2,3,4,5-tetrahydro-1H-benzo[d]azepine hydrochloride

Dissolve crude 6-methoxy-2,3,4,5-tetrahydro-1H-benzo[d]azepine (35.1 g, 0.198 mol) in ethanol (250 mL). Heat the solution to reflux and add 2 N HCl in ethanol (108.9 mL, 0.218 mol, 1.1 equiv.). Slowly add heptane (700 mL) over 10 min, then remove the heating mantle and cool the solution to RT and finally continue the cooling with an ice water mixture. Collect the resulting solid by vacuum filtration and wash with cold 1:2 ethanol:heptane (3×100 mL), dry for 15 min while applying vacuum suction, then further dry the product in a vacuum oven at 60° C. for 1 h to give the title compound as a white granular solid (35.53 g, 63%).
$^1$H NMR (300 MHz, DMSO-d6) δ 9.82 (br s, 1H), 7.12 (dd, 1H, J=7.6, 7.9), 6.88 (d, 1H J=8.2), 6.78 (d, 1H, J=7.3), 3.75 (s, 3H), 3.20-3.00 (m, 8H); $^{13}$C NMR (300 MHz, DMSO-d6) δ 156.2, 141.3, 127.4, 127.2, 121.6, 109.7, 55.7, 44.9, 44.7, 31.6, 21.7; MS (ES): m/z=178 [M+H]; mp 246.6-246.9° C.; Anal. Calc'd for C$_{11}$H$_{15}$ClNO: C, 62.12; H, 7.11; N, 6.59. Found: C, 61.95, H, 7.64; N, 6.58.

6-Methoxy-3-(2,2,2-trifluoroacetyl)-2,3,4,5-tetrahydro-1H-benzo[d]azepine

To a slurry of 6-methoxy-2,3,4,5-tetrahydro-1H-benzo[d]azepine hydrochloride (35.3 g, 0.165 mol, 1 equiv.) and triethylamine (69.1 µL, 0.496 mol, 3 equiv.) in DCM (300 mL) cooled at 0° C. with ice water, add dropwise a solution of trifluoroacetic anhydride (25.7 µL, 0.182 mol, 1.1 equiv.) in DCM (40 mL) over 30 min, but at a rate that maintains the temperature below 10° C. After the addition is complete, warm the reaction mixture to RT and stir until the reaction is complete by TLC (about 2 hr). Wash the solution with water (2×350 mL), and then brine (350 mL), dry (sodium sulfate) filter and concentrate to give the title compound as a yellow oil that solidifies upon standing (44.9 g, 96%). Use the material without further purification in the next step. Prepare an analytical sample utilizing silica gel chromatography, eluting with 40:60 diethyl ether:hexanes.
$^1$H NMR (300 MHz, CDCl$_3$) δ 7.16-7.11 (m, 1H), 6.81-6.74 (m, 2H), 3.81 (s, 3H), 3.79-3.64 (m, 4H), 3.11-3.07 (m, 2H), 2.99-2.95 (m, 2H); $^1$H NMR (300 MHz, DMSO-d6) δ 7.13 (dd, 1H, J=1.5, 7.0), 7.08 (d, 1H, J=1.5), 6.88-6.74 (m, 1H), 3.75 (s, 3H), 3.67-3.61 (m, 4H), 3.04-2.92 (m, 4H); $^{13}$C NMR (300 MHz, DMSO-d6) δ 156.38. 156.43. 155.06, 155.00, 154.60, 154.54, 154.14, 154.08, 141.31, 141.04, 127.44, 127.18, 127.05, 127.01, 122.27, 121.94, 121.90, 118.46, 114.64, 110.80, 109.52, 109.41, 55.63, 55.61, 47.11, 47.07, 46.67, 46.63, 45.61, 45.16, 35.90, 34.65, 26.18, 24.91; mp 74-76° C.; Anal. Calc'd for $C_{13}H_{14}F_3NO_2$: C, 57.14; H, 5.16; N, 5.13. Found: C, 57.17, H, 5.27; N, 5.08.

6-Hydroxy-3-(2,2,2-trifluoroacetyl)-2,3,4,5-tetrahydro-1H-benzo[d]azepine

To a 1 M solution of $BBr_3$ (1.1 L, 1.6 equiv.), cooled at 0° C. with an ice water bath, add 6-methoxy-3-(2,2,2-trifluoroacetyl)-2,3,4,5-tetrahydro-1H-benzo[d]azepine (187 g, 0.684 mol) in DCM (200 mL) over 1 hr, while maintaining the temperature between 0° C. and 10° C. Warm the reaction mixture to RT and stir until HPLC indicates completion of the reaction (about 2 h.). Cool the solution to 0° C. and transfer it via cannula into an ice water solution (1.2 L), thereby precipitating the product as a white solid. Add EtOAc (2 L) to dissolve most of the precipitate, separate the layers and concentrate the organic layer. Extract the aqueous layer three times with EtOAc (2×2 L, 1×1 L). Wash the combined organic layers with water (2 L), and then brine (2 L), dry (sodium sulfate) and concentrate to give the title compound as a light yellow solid (166.3 g, 94%). Use the product for the next step without further purification. Prepare an analytical sample utilizing silica gel chromatography, eluting with 40:60 diethyl ether:hexanes.
$^1$H NMR (300 MHz, DMSO-d6) δ 9.39 (s, 1H), 6.94-6.88 (m, 1H), 6.72-6.68 (m, 1H), 6.61-6.57 (m, 1H), 3.67-3.32 (m, 4H), 2.99-2.86 (m, 4H); $^{13}$C NMR (300 MHz, DMSO-d6) 6154.50, 141.47, 141.18, 126.77, 126.64, 125.77, 125.33, 120.38, 120.32, 118.49, 114.67, 113.64, 113.47, 47.31, 47.27, 47.00, 46.96, 45.83, 45.49, 36.17, 34.93, 26.46, 25.18, 20.66, 14.00; MS (ES): m/z=260 [M+H]; mp 183.0-185.2° C.; Anal. Calc'd. for $C_{12}H_{12}F_3NO_2$: C, 55.60; H, 4.67; N, 5.40. Found: C, 55.51, H, 4.71; N, 5.29.

7-Chloro-6-hydroxy-3-(2,2,2-trifluoroacetyl)-2,3,4,5-tetrahydro-1H-benzo[d]azepine Heat a mixture of 6-hydroxy-3-(2,2,2-trifluoroacetyl)-2,3,4,5-tetrahydro-1H-benzo[d]azepine (120 g, 0.4629 mol) and toluene (14.4 L) to 70° C. for 45 min until most of the starting material is dissolved. Add diisobutylamine (1.197 g, 1.62 mL, 9.26 mmol) followed by addition of sulfuryl chloride (62.48 g, 37.19 mL, 0.463 mol) in toluene (360 mL) over 20 min. Stir the reaction mixture for 50 min and then add additional sulfuryl chloride (4.536 g, 2.70 mL, 0.0336 mol) neat and stir the reaction mixture for 15 min at 70° C. Cool the reaction mixture to 24° C. over 30 min and then add 1 N HCl (2.00 L). Separate, wash the organic layer with saturated aqueous sodium bicarbonate solution (2.00 L), brine (2.00 L), dry (sodium sulfate) and concentrate using a rotary evaporator at 70° C. until about 672.5 g remains using the minimum effective vacuum in order to maintain a vapor phase sufficient to prevent drying above the solvent line and self-seeding, thus preventing crystallization under these conditions. Using toluene heated to 70° C., transfer the light-yellow solution to a preheated (70° C.) 3-neck flask equipped with a mechanical stirrer. Lower the temperature to 58° C. over 1 h. If available, seed the solution with crystals of 7-chloro-6-hydroxy-3-(2,2,2-trifluoroacetyl)-2,3,4,5-tetrahydro-1H-benzo[d]azepine from a prior synthesis to enhance crystallization. After 30 min, reduce the temperature further to 55° C. and observe the initiation of the crystallization process. Hold the temperature at 55° C. for 2 h followed by 4 h at 45° C., then turn off the heat allowing the mixture to slowly reach 24° C. (RT). After stirring for 8 h with the heat off, cool the mixture to 0° C. for 2 hr, followed by 2 h at −10° C. Collect the resulting dense, white, granular crystals by vacuum filtration at −10° C. Rinse the crystals twice with cold (−10° C.) toluene and vacuum dry at 50° C., 5 Torr, for 12 hr, to give the title compound as a white solid (120.7 g, 99.5% purity, 88.8%).
MS (ES): m/z=294 [M+H]; mp 133-134° C.; Anal. Calc'd for $C_{12}H_{11}ClF_3NO_2$: C, 49.08; H, 3.78. N, 4.77. Cl, 12.07. Found: C, 49.01. H, 3.63. N, 4.720 Cl, 12.32.

7-Chloro-3-(2,2,2-trifluoroacetyl)-6-trifluoromethanesulfonyloxy-2,3,4,5-tetrahydro-1H-benzo[d]azepine Cool a solution of 7-chloro-6-hydroxy-3-(2,2,2-trifluoroacetyl)-2,3,4,5-tetrahydro-1H-benzo[d]azepine (60 g, 0.204 mol), triethylamine (62.6 mL, 0.448 mol, 2.2 equiv.), and DCM (590 mL) in an ice bath and add dropwise trifluoromethanesulfonic anhydride (43.5 mL, 0.258 mol, 1.26 equiv.) over 70 min. Remove the ice bath and stir the reaction mixture for 2 h. Wash the reaction mixture sequentially with water (500 mL), 1 N HCl (500 mL), water (500 mL), and brine (500 mL). Dry (sodium sulfate) and concentrate to give the crude product as a brown solid (90 g). Dissolve the solid in warm toluene (200 mL). Further purify by plug filtration silica gel chromatography (500 g) eluting sequentially with hexanes (1 L), 9:1 hexanes:EtOAc (1 L), 4:1 hexanes:EtOAc (1 L), and 7:3 hexanes:EtOAc (9 L). Pool the eluents and concentrate to obtain the product as a yellow tan solid (86.3 g). Dissolve the solid in warm EtOAc (86 mL) and then add hexanes (700 mL). If available, seed the solution with crystals of 7-chloro-3-(2,2,2-trifluoroacetyl)-6-trifluoromethanelsulfonyloxy-2,3,4,5-tetrahydro-1H-benzo[d]azepine from a prior synthesis to enhance crystallization. Allow the mixture to stand at RT for 30 min. Cool the mixture to about −10° C. for 2 hr, filter, rinse the crystals with cold (−10° C.) hexanes:EtOAc, and air dry under vacuum to obtain the title compound as a first crop of crystals (73.54 g). Concentrate the mother liquor to obtain a solid (12.7 g). Recrystallize the solid in a mixture of EtOAc/hexanes (15 mL: 121 mL) to obtain additional title compound (7.65 g, total yield: 81.19 g, 93%).

Preparation 2

3-tert-Butoxycarbonyl-7-chloro-6-(1'-benzhydrylidene-hydrazino)-2,3,4,5-tetrahydro-1H-benzo[d]azepine

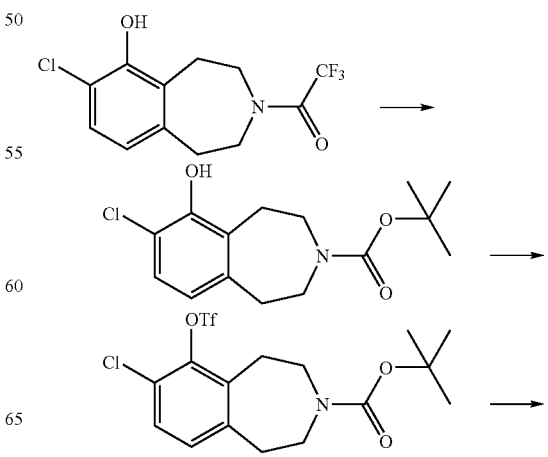

3-tert-Butoxycarbonyl-7-chloro-6-(N'-benzhydrylidene-hydrazino)-2,3,4,5-tetrahydro-1H-benzo[d]azepine Dissolve 3-tert-butoxycarbonyl-7-chloro-6-trifluoromethanesulfonyloxy-2,3,4,5-tetrahydro-1H-benzo[d]azepine (4.39 g, 10.2 mmol) in dry, degassed toluene (100 mL) under nitrogen, then add benzophenone hydrazone (2.00 g, 10.2 mmol), sodium tert-butoxide (1.37 g, 14.3 mmol), BINAP (635 mg, 1.02 mmol) and bis(dibenzylideneacetone) palladium (0) (280 mg, 0.306 mmol). Stir at 100° C. for 8 hr, cool to RT, concentrate and purify (silica gel chromatography, eluting with 95:5 2-methylpentane:EtOAc) to give the title compound (4.2 g, 87%).

MS (ES): m/z=476 [M+H].

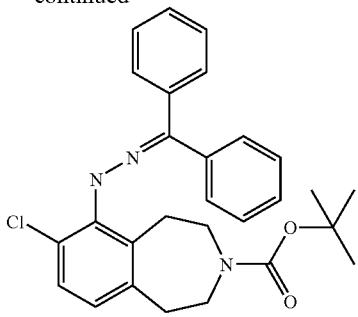

3-tert-Butoxycarbonyl-7-chloro-6-hydroxy-2,3,4,5-tetrahydro-1H-benzo[d]azepine Dissolve 7-chloro-3-(2,2,2-trifluoroacetyl)-6-hydroxy-2,3,4,5-tetrahydro-1H-benzo[d]azepine (2.0 g, 6.80 mmol) in methanol (100 mL). Add potassium carbonate (14.08 g, 102 mmol) in water (50 mL) slowly. Stir the reaction at RT for 2 h, add tert-butoxycarbonyl anhydride (1.59 g, 7.48 mmol) in DCM (70 mL) and stir vigorously for 17 h. Concentrate the organic layer, wash the aqueous layer with DCM (3×50 mL), combine the organic layers, dry (MgSO₄) and concentrate to give the title compound (2.12 g, 100%).

MS (ES): m/z=320 [M+Na].

3-tert-Butoxycarbonyl-7-chloro-6-trifluoromethanesulfonyloxy-2,3,4,5-tetrahydro-1H-benzo[d]azepine Add to a solution of 3-tert-butoxycarbonyl-7-chloro-6-hydroxy-2,3,4,5-tetrahydro-1H-benzo[d]azepine (328 mg, 1.1 mmol) in dry DCM (20 mL) at 0° C. under nitrogen, pyridine (2 mL), followed by trifluoroacetic anhydride (0.37 mL, 2.2 mmol) slowly. Stir the reaction at RT for 2 h, quench with 2 N HCl (10 mL). Wash the organic layer with saturated aqueous sodium bicarbonate (10 mL), dry (MgSO₄) and concentrate to give the title compound as a white powder (368 mg, 78%).

Preparation 3

(2E)-3-(Dimethylamino)-1-thien-3-ylprop-2-en-1-one

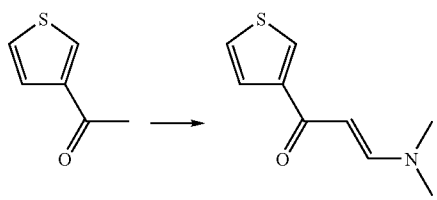

Stir 1-thien-3-ylethanone (1.26 g, 10 mmol) with N,N-dimethylformamide dimethyl acetal (2.66 mL, 20 mmol) at reflux for 4 h. Cool to RT, concentrate and dry in a vacuum oven to give the title compound as a brown solid (1.27 g, 70%).

MS (ES): m/z=183 [M+H].

The compounds of Preparations 4-20 may be prepared essentially as described in Preparation 3 by using the appropriate ethanone.

| Prep | Compound Structure | Compound Name | MS (ES) [M + H] |
|------|--------------------|---------------|-----------------|
| 4 | (phenyl enaminone structure) | (2E)-3-(Dimethylamino)-1-phenylprop-2-en-1-one | 176 |
| 5 | (2-CF₃ phenyl enaminone structure) | (2E)-3-(Dimethylamino)-1-[2-(trifluoromethyl)phenyl]prop-2-en-1-one | 244 |
| 6 | (3-CF₃ phenyl enaminone structure) | (2E)-3-(Dimethylamino)-1-[3-(trifluoromethyl)phenyl]prop-2-en-1-one | 244 |

-continued

| Prep | Compound Structure | Compound Name | MS (ES) [M + H] |
|---|---|---|---|
| 7 | 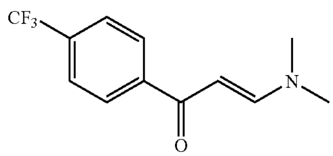 | (2E)-3-(Dimethylamino)-1-[4-(trifluoromethyl)phenyl]prop-2-en-1-one | 244 |
| 8 | 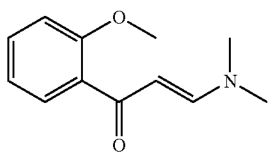 | (2E)-3-(Dimethylamino)-1-[2-(methoxy)phenyl]prop-2-en-1-one | 206 |
| 9 | 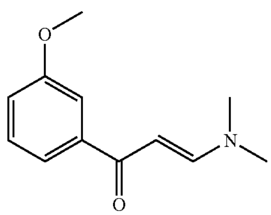 | (2E)-3-(Dimethylamino)-1-[3-(methoxy)phenyl]prop-2-en-1-one | 206 |
| 10 | 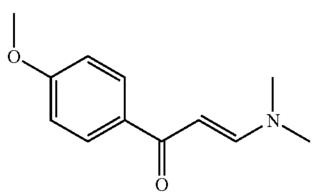 | (2E)-3-(Dimethylamino)-1-[4-(methoxy)phenyl]prop-2-en-1-one | 206 |
| 11 | 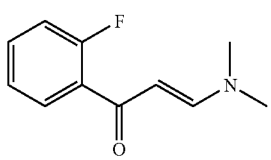 | (2E)-3-(Dimethylamino)-1-[2-fluorophenyl]prop-2-en-1-one | 194 |
| 12 | 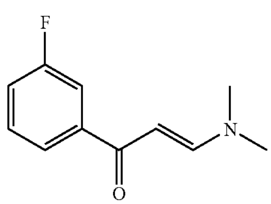 | (2E)-3-(Dimethylamino)-1-[3-fluorophenyl]prop-2-en-1-one | 194 |
| 13 | 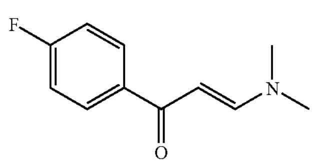 | (2E)-3-(Dimethylamino)-1-[4-fluorophenyl]prop-2-en-1-one | 194 |
| 14 | 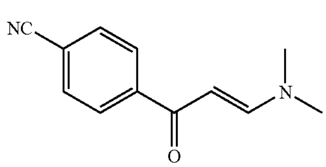 | (2E)-3-(Dimethylamino)-1-[4-cyanophenyl]prop-2-en-1-one | 201 |

| Prep | Compound Structure | Compound Name | MS (ES) [M + H] |
|---|---|---|---|
| 15 | 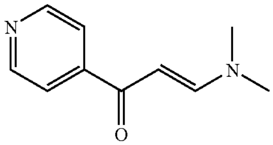 | (2E)-3-(Dimethylamino)-1-(4-pyridyl)prop-2-en-1-one | 177 |
| 16 | 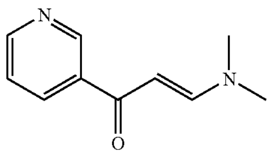 | (2E)-3-(Dimethylamino)-1-(3-pyridyl)prop-2-en-1-one | 177 |
| 17 | 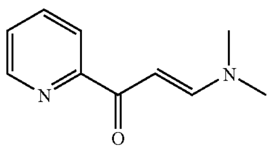 | (2E)-3-(Dimethylamino)-1-(2-pyridyl)prop-2-en-1-one | 177 |
| 18 | 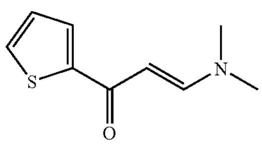 | (2E)-3-(Dimethylamino)-1-thien-2-ylprop-2-en-1-one | 182 |
| 19 | 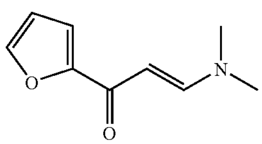 | (2E)-3-(Dimethylamino)-1-furan-2-ylprop-2-en-1-one | 166 |
| 20 | 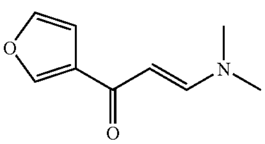 | (2E)-3-(Dimethylamino)-1-furan-3-ylprop-2-en-1-one | 166 |

Preparation 21

1-(Phenylthio)pentane-2,4-dione

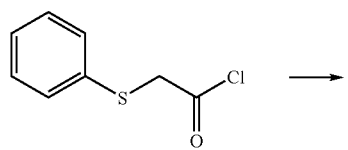

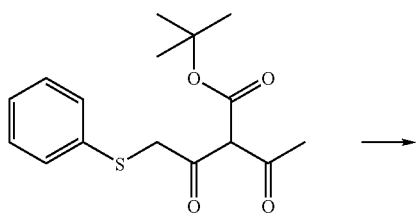

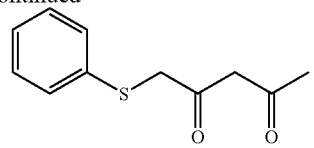

1,1-Dimethylethyl 2-acetyl-3-oxo-4-(phenylthio)butanoate Add tert-butyl acetoacetate (1.30 mL, 8.0 mmol) dropwise to a solution of sodium tert-butoxide (770 mg, 8.0 mmol) in diethyl ether (15 mL) at 0° C. under nitrogen. Stir the white precipitate at RT for 20 h and cool to 0° C. Add (phenylthio)acetyl chloride (1.2 mL, 8.0 mmol) dropwise and observe as the suspension turns yellow, then becomes a clear solution, and finally forms a white precipitate when all the reagent is added. Stir the reaction for 24 h at RT. Quench with 2 N HCl (15 mL), wash the aqueous layer with EtOAc (15 mL). Dry (MgSO$_4$), concentrate and purify (silica gel chromatography, eluting with 100:0 to 90:10 2-methylpentane: EtOAc) to give the title compound as light yellow solid (1.11 g, 48%)

MS (ES): m/z=307 [M−H].

1-(Phenyltlhio)pentane-2,4-dione Stir 1,1-dimethylethyl 2-acetyl-3-oxo-4-(phenylthio)butanoate (1.11 g, 3.60 mmol) in TFA (3 mL) for 20 h at RT. Quench with water (10 mL), and extract using diethyl ether (10 mL). Wash organic layer with water (3×10 mL), dry (MgSO$_4$), concentrate and purify (silica gel chromatography, eluting with 100:0 to 80:20 2-methylpentane:EtOAc) to give the title compound as an orange oil (513 mg, 69%).

The compounds in Preparation 22-28 may be prepared essentially as described in Preparation 21 by using the appropriate acetyl chloride.

| Prep | Compound Structure | Compound Name | GC-MS [M+] |
|---|---|---|---|
| 22 | 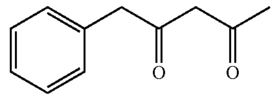 | 1-Phenylpentane-2,4-dione | 176 |
| 23 | 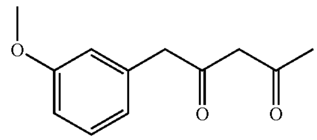 | 1-(3-Methoxyphenyl)pentane-2,4-dione | |
| 24 | 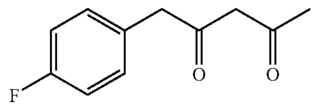 | 1-(4-Fluorophenyl)pentane-2,4-dione | 194 |
| 25 | 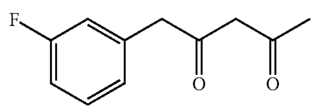 | 1-(3-Fluorophenyl)pentane-2,4-dione | 194 |
| 26 | 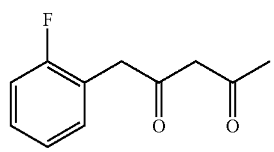 | 1-(2-Fluorophenyl)pentane-2,4-dione | 194 |
| 27 | 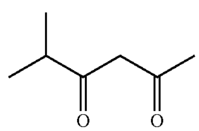 | 5-Methylhexane-2,4-dione | |
| 28 | 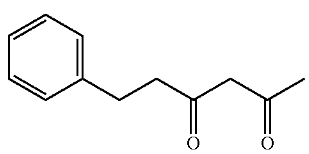 | 6-Phenylhexane-2,4-dione | |

Preparation 29

2-Phenylazetidine

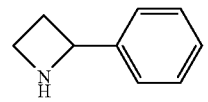

Add lithium aluminum hydride (685 mg, 18.1 mmol) to anhydrous ether (20 mL), followed by 4-phenyl-2-azetidinone (760 mg, 5.2 mmol). Heat the mixture to reflux for 4 hr, cool to RT. Add 20% aqueous ammonium chloride solution to quench the reaction, filter through Celite®, concentrate and purify (silica gel chromatography, eluting with 10:90 2 M ammonia in methanol:DCM) to give the title compound as a colorless oil (380 mg, 55%).

$^1$H NMR (400 MHz, CDCl$_3$) δ 7.42-7.22 (m, 5H), 4.97 (t, J=8.3 Hz, 1H), 3.82-3.76 (m, 1H), 3.44-3.39 (m, 1H), 2.60-2.38 (m, 3H).

Preparation 30

7-Chloro-6-(3-hydroxy-2,2-dimethyl-propylamino)-3-(2,2,2-trifluoroacetyl)-2,3,4,5-tetrahydro-1H-benzo[d]azepine

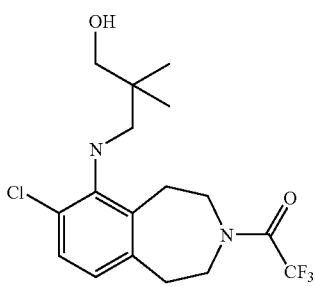

2,2-Dimethyl-3-(tetrahydro-pyran-2-yloxy)-propylamine Dissolve 3-amino-2,2-dimethyl-1-propanol (2.063 g, 20 mmol) in DCM (100 mL), add 3,4-dihydro-2H-pyran (4.04 g, 48 mmol) and p-toluensulfonic acid monohydrate (4.185 g, 22 mmol). Stir the reaction at RT overnight. Basify with 1 N NaOH solution, separate the organic layer, and extract the aqueous layer with DCM three times. Combine the organic layers, wash with brine, dry (sodium sulfate) concentrate and purify (silica gel chromatography, eluting with 5:95 2 M ammonia in methanol:DCM) to give the title compound as a colorless oil (1.574 g, 42%).

MS (ES): m/z:=188.1 [M+H].

7-Chloro-6-[2,2-dimethyl-3-(tetrahydro-pyran-2-yloxy)-propylamino]-3-(2,2,2-trifluoroacetyl)-2,3,4,5-tetrahydro-1H-benzo[d]azepine Mix 7-chloro-3-(2,2,2-trifluoroacetyl)-6-trifluoromethanesulfonyloxy-2,3,4,5-tetrahydro-1H-benzo[d]azepine (1.277 g, 3.0 mmol), 2,2-dimethyl-3-(tetrahydro-pyran-2-yloxy)-propylamine (843 mg, 4.5 mmol), palladium acetate (135 mg, 0.6 mmol), BINAP (1.308 g, 2.1 mmol), bis(dibenzylideneacetone)palladium (0) (275 mg, 0.3 mmol) and cesium carbonate (1.955 g, 6.0 mmol) in anhydrous toluene (75 mL), degas, heat at 90° C. for 16 h. Filter off solid through Celite®, concentrate and purify (silica gel chromatography, eluting with 1:7 EtOAc:hexanes) to give the title compound (1.190 g, 86%).

MS (ES): m/z:=463.2 [M+H].

7-Chloro-6-(3-hydroxy-2,2-dimethyl-propylamino)-3-(2,2,2-trifluoroacetyl)-2,3,4,5-tetrahydro-1H-benzo[d]azepine Add p-toluensulfonic acid monohydrate (538 mg, 2.83 mmol) to a solution of 7-chloro-6-[2,2-dimethyl-3-(tetrahydro-pyran-2-yloxy)-propylamino]-3-(2,2,2-trifluoroacetyl)-2,3,4,5-tetrahydro-1H-benzo[d]azepine (1.190 g, 2.57 mmol) in methanol (80 mL). Stir the reaction at RT for 16 hr, concentrate, redissolve in EtOAc, wash with saturated aqueous sodium bicarbonate solution, brine, dry (sodium sulfate), concentrate and purify (silica gel chromatography, eluting with 1:4 EtOAc:hexanes) to give the title compound (750 mg, 79%).

MS (ES): m/z=379.2 [M+H].

Preparation 31

3-(2,2,2-Trifluoroacetyl)-6-trifluoromethanesulfonyloxy-7-trifluoromethyl-2,3,4,5-tetrahydro-1H-benzo[d]azepine

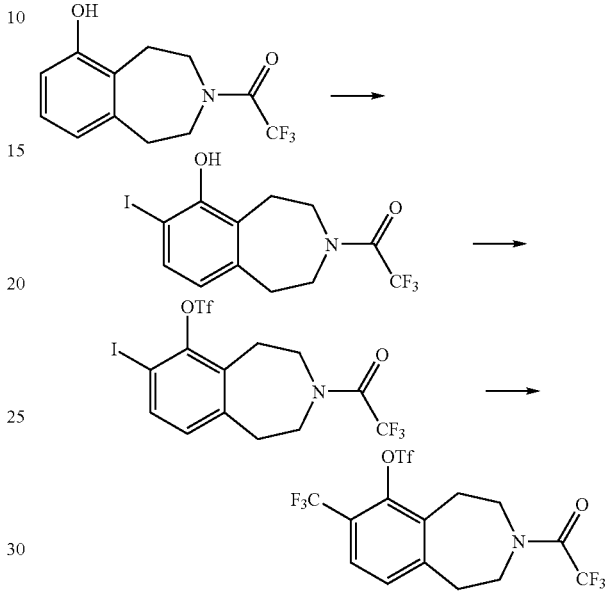

6-Hydroxy-7-iodo-3-(2,2,2-trifluoroacetyl)-2,3,4,5-tetrahydro-1H-benzo[d]azepine Add 6-hydroxy-3-(2,2,2-trifluoroacetyl)-2,3,4,5-tetrahydro-1H-benzo[d]azepine (1.037 g, 4.0 mmol) and diisopropylamine (60.7 mg, 0.6 mmol) to anhydrous DCM (350 mL) and stir at 10-20° C. Add slowly a solution of N-iodosuccinimide (1.035 g, 4.6 mmol) in DCM (100 mL) over a period of 3 h. Stir the reaction mixture overnight and gradually warm to RT. Quench the reaction with saturated aqueous sodium bicarbonate, separate the organic layer, wash the organic layer with 0.1 N HCl, brine, dry (sodium sulfate) concentrate and purify (silica gel chromatography, eluting with 5:95 to 10:90 EtOAc:hexanes) to give the title compound as a white solid (1.0 g, 65%).

MS (ES): m/z=386 [M+H].

7-Iodo-3-(2,2,2-trifluoroacetyl)-6-trifluoromethanesulfonyloxy-2,3,4,5-tetrahydro-1H-benzo[d]azepine Add triethylamine (496 mg, 4.90 mmol) to a solution of 6-hydroxy-7-iodo-3-(2,2,2-trifluoroacetyl)-2,3,4,5-tetrahydro-1H-benzo[d]azepine (945 mg, 2.45 mmol) in DCM (30 mL) at 0° C. Add dropwise trifluoromethanesulfonic anhydride (1.244 g, 4.41 mmol) and stir at 0° C. for 1 h. Warm to RT overnight. Dilute the mixture with DCM, wash with water, saturated aqueous sodium bicarbonate solution and brine. Dry (sodium sulfate), concentrate and purify (silica gel chromatography, eluting with 1:6 EtOAc:hexanes) to give the title compound as a white solid (1.246 g, 98%).

MS (ES): m/z=518 [M+H].

3-(2,2,2-Trifluoroacetyl)-6-trifluoromethanesulfonyloxy-7-trifluoromethyl-2,3,4,5-tetrahydro-1H-benzo[d]azepine Add copper (I) iodide (367 mg, 1.93 mmol), methyl 2,2-difluoro-2-(fluorosulfonyl)acetate (1.852 g, 9.64 mmol) and HMPA (1.728 g, 9.64 mmol) to a solution of 7-iodo-3-(2,2,2-trifluoroacetyl)-6-trifluoromethanesulfonyloxy-2,3,4,5-tetrahydro-1H-benzo[d]azepine (1.246 g, 2.41 mmol) in DMF (8 mL) and heat the mixture at 70° C. for 1.5 h. Add same amount of copper (I) iodide, methyl 2,2-difluoro-2-(fluorosulfonyl)acetate, and HMPA and stir further for 4 h. Cool the mixture to RT, quench with saturated aqueous ammonium chloride solution, separate the organic layer, and extract the aqueous layer with EtOAc three times. Combine the organic layers, wash with saturated aqueous sodium bicarbonate solution, brine, dry (sodium sulfate), concentrate and purify (silica gel chromatography, eluting with 5:95 to 10:90 EtOAc:hexanes) to give the title compound as a white solid (321 mg, 29%) and to recover the starting material (741 mg, 59%).

MS (ES): m/z=460 [M+H].

Preparation 32

7-Ethyl-3-(2,2,2-trifluoroacetyl)-6-trifluoromethanesulfonyloxy-2,3,4,5-tetrahydro-1H-benzo[d]azepine

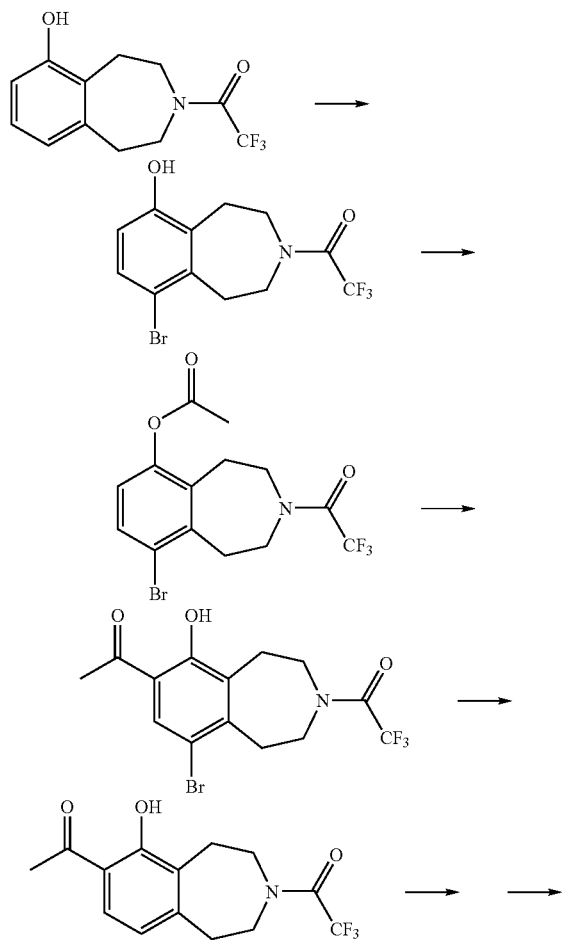

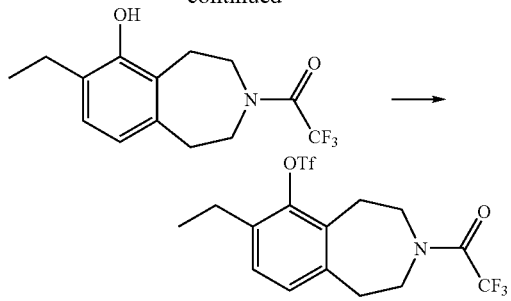

9-Bromo-6-hydroxy-3-(2,2,2-trifluoroacetyl)-2,3,4,5-tetrahydro-1H-benzo[d]azepine Add dropwise bromine (10.8 mL, 0.21 mol) in acetonitrile (260 mL) to a slurry of 6-hydroxy-3-(2,2,2-trifluoroacetyl)-2,3,4,5-tetrahydro-1H-benzo[d]azepine (51.8 g, 0.2 mol) in acetonitrile (400 mL) at 0° C. cooling with ice-water to keep the temperature between 2-5° C. Warm the reaction to RT and stir for 30 min. Pour the mixture into ice cold water (2 L) to obtain a white precipitate. Collect the solid by vacuum filtration, wash with water and dry under vacuum at 105° C. Recrystallize the crude material in toluene/heptane and cool the mixture in an ice bath. Collect the solid by vacuum filtration, wash with heptane and dry under vacuum at 105° C. to obtain the desired intermediate as a white solid (54.63 g, 81%).

MS (ES): m/z=338 [M+H].

6-Acetoxy-9-bromo-3-(2,2,2-trifluoroacetyl)-2,3,4,5-tetrahydro-1H-benzo[d]azepine Under a nitrogen atmosphere, mix 9-bromo-6-hydroxy-3-(2,2,2-trifluoroacetyl)-2,3,4,5-tetrahydro-1H-benzo[d]azepine (6 g, 17.8 mmol), anhydrous pyridine (0.06 mL, 0.72 mmol), 4-(dimethylamino)pyridine (222 mg, 1.8 mmol) and acetic anhydride (30 mL). Heat the mixture at reflux for 8 h and stir at RT for another 8 h Concentrate, dilute the residue in EtOAc, wash with 1 N HCl, and then with saturated aqueous sodium bicarbonate solution. Dry (sodium sulfate) and concentrate to give the title compound that was used in the next step without further purification.

MS (ES): m/z=380 [M+H].

7-Acetyl-9-bromo-6-hydroxy-3-(2,2,2-trifluoroacetyl)-2,3,4,5-tetrahydro-1H-benzo[d]azepine Under a nitrogen atmosphere, mix 6-acetoxy-9-bromo-3-(2,2,2-trifluoroacetyl)-2,3,4,5-tetrahydro-1H-benzo[d]azepine (2.8 g, 7.4 mmol) and nitrobenzene (5 mL). Add anhydrous aluminum chloride (980 mg, 7.4 mmol). Heat at 180° C. for 2 h. Cool the mixture to RT. Add concentrated HCl (10 mL) dropwise. Stir the mixture for 30 min. Add 1 N HCl then extract with EtOAc. Dry (sodium sulfate), concentrate and purify (silica gel chromatography, eluting with 0:100 to 10:80 EtOAc:hexanes) to give the title compound (833 mg, 30%).

MS (ES): m/z=378 [M−H].

7-Acetyl-6-hydroxy-3-(2,2,2-trifluoroacetyl)-2,3,4,5-tetrahydro-1H-benzo[d]azepine Mix 7-acetyl-9-bromo-6-hydroxy-3-(2,2,2-trifluoroacetyl)-2,3,4,5-tetrahydro-1H-benzo[d]azepine (833 mg, 2.2 mmol), tetrakis(triphenylphosphine)palladium(0) (150 mg, 0.13 mmol) and sodium formate (224 mg, 3.3 mmol) in anhydrous DMF (15 mL). Degas twice then flush with argon. Keep the flask under argon and heat the reaction at 95° C. for 16 h. Dilute with EtOAc then wash with 1 N HCl. Separate the organic layer, dry (sodium sulfate), concentrate and purify (silica gel chromatography, eluting with 1:100 to 20:80 EtOAc:hexanes) to give the title compound (448 mg, 68%).

MS (ES): m/z=302 [M+H].

7-Ethyl-6-hydroxy-3-(2,2,2-trifluoroacetyl)-2,3,4,5-tetrahydro-1H-benzo[d]azepine Under nitrogen dissolve 7-acetyl-6-hydroxy-3-(2,2,2-trifluoroacetyl)-2,3,4,5-tetrahydro-1H-benzo[d]azepine (1.0 g, 3.32 mmol) in anhydrous THF (100 mL). Cool the solution to 0° C., add boron trifluoride diethyl etherate (3.4 mL, 26.6 mmol) and sodium cyanoborohydride (836 mg, 13.3 mmol). Remove the ice bath and stir for 5 h at RT. Dilute with EtOAc and wash with 0.1 N HCl. Separate the organic layer, dry (sodium sulfate) and concentrate. MS (ES): m/z=302 [M–H]. Mix the residue with trifluoroacetic acid (40 mL) and anhydrous DCM (50 mL) under nitrogen. Cool to 0° C. in an ice bath and add triethylsilane (3.5 mL, 21.9 mmol). After 15 min, remove the ice bath and stir at RT for 16 h. Concentrate and purify (silica gel chromatography, eluting with 10:90 EtOAc:hexanes to give the title compound (698 mg, 73%).

MS (ES): m/z=286 [M–H].

7-Ethyl-3-(2,2,2-trifluoroacetyl)-6-trifluoromethanesulfonyloxy-2,3,4,5-tetrahydro-1H-benzo[d]azepine Under nitrogen mix 7-ethyl-6-hydroxy-3-(2,2,2-trifluoroacetyl)-2,3,4,5-tetrahydro-1H-benzo[d]azepine (698 mg, 2.4 mmol), triethylamine (0.67 mL, 4.8 mmol) and anhydrous DCM (25 mL). Cool the mixture in an ice bath, add dropwise trifluoromethanesulfonic anhydride (0.81 mL, 4.8 mmol) and stir at RT for 3 h. Quench with water and extract three times with DCM. Wash the organic extracts with 0.1 N HCl and brine. Dry (sodium sulfate) and concentrate to give the title compound (1.0 g, 100%).

MS (ES): m/z=420 [M+H].

Preparation 33

7-Chloro-6-(3-hydroxyazetidin-1-yl)-3-(2,2,2-trifluoroacetyl)-2,3,4,5-tetrahydro-1H-benzo[d]azepine

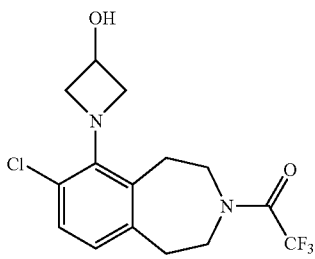

1-Benzhydryl-3-(tert-butyl-dimethylsilanyloxy)-azetidine

Under nitrogen dissolve 1-benzhydrylazetan-3-ol (5 g, 20.9 mmol), imidazole (3.5 g, 52.25 mmol) in anhydrous DMF (25 mL). Cool solution in an ice bath, add slowly tert-butyldimethylsilyl chloride (50 wt. % solution in toluene, 6.3 g, 41.8 mmol). Stir at RT for 22 h. Dilute with EtOAc and wash with saturated aqueous sodium bicarbonate solution. Separate organic layer, dry (sodium sulfate), concentrate and purify (silica gel chromatography, eluting with 10:90 EtOAc:hexanes) to give the title compound (3.89 g, 53%).

MS (ES): m/z=354.2 [M+H].

3-(tert-Butyl-dimethylsilanyloxy)-azetidine

Add 20% palladium hydroxide on activated carbon (0.946 g) and ethanol (20 mL) to a Parr pressure vessel. Purge the reaction vessel with nitrogen, pressurize the reaction mixture with hydrogen (400 kPa), seal the vessel and agitate the mixture at RT for 15 min. Vent the hydrogen from the reaction vessel and purge the reaction vessel with nitrogen. Add 1-benzhydryl-3-(tert-butyl-dimethylsilanyloxy)-azetidine (3.89 g, 0.0110 mol) and ethanol (80 mL) to the pressure vessel. Purge the reaction vessel with nitrogen, pressurize the reaction mixture with hydrogen (400 kPa), seal the vessel and agitate the reaction at RT for 6 h. Turn off the agitation, vent the excess hydrogen from the vessel and purge the vessel with nitrogen. Sample the reaction mixture for analysis. Once the reaction is shown to be complete, filter the reaction mixture to remove the catalyst, concentrate and purify (silica gel chromatography, eluting with 5:95 to 10:90 2 M ammonia in methanol: DCM) to give the title compound (889 mg, 43%).

MS (ES): m/z=188.1 [M+H].

7-Chloro-6-[3-(tert-butyldimethyl-silanyloxy)-azetidin-1-yl]-3-(2,2,2-trifluoroacetyl)-2,3,4,5-tetrahydro-1H-benzo[d]azepine Use 7-chloro-3-(2,2,2-trifluoroacetyl)-6-trifluoromethanesulfonyloxy-2,3,4,5-tetrahydro-1H-benzo[d]azepine (prepared essentially as described in Preparation 1)(979 mg, 2.3 mmol), 3-(tert-butyldimethyl-silanyloxy)-azetidine (880 mg, 4.7 mmol), palladium (II) acetate (51.6 mg, 0.23 mmol), tris(dibenzylideneacetone)dipalladium(0) (211 mg, 0.23 mmol), BINAP (racemic, 215 mg, 0.345 mmol), cesium carbonate (1.1 g, 3.45 mmol), anhydrous toluene (50 mL) and degas and fill with nitrogen (3 times). Seal the system with septum and tighten it with copper wire when necessary. Heat the mixture at 95° C. for 8 h. Dilute with EtOAc, wash with saturated aqueous sodium bicarbonate solution, brine, dry (sodium sulfate), concentrate and purify (silica gel chromatography, eluting with 10:90 EtOAc:hexanes) to give the title compound (763 mg, 72%).

MS (ES): m/z:=463.1 [M+H].

7-Chloro-6-(3-hydroxyazetidin-1-yl)-3-(2,2,2-trifluoroacetyl)-2,3,4,5-tetrahydro-1H-benzo[d]azepine Under nitrogen mix 7-chloro-6-[3-(tert-butyldimethyl-silanyloxy)-azetidin-1-yl]-3-(2,2,2-trifluoroacetyl)-2,3,4,5-tetrahydro-1H-benzo[d]azepine (594 mg, 1.29 mmol), 1 N tetrabutylammonium fluoride solution in THF (2.04 mL, 2.04 mmol), glacial acetic acid (0.2 mL, 3.33 mmol), 4 Å molecular sieve (650 mg) in anhydrous THF (18 mL). Stir at RT for 3 days. After the first day add more 1 N tetrabutylammonium fluoride solution in THF (2.04 mL, 2.04 mmol) and glacial acetic acid (0.2 mL, 3.33 mmol). After the second day add more 1 N tetrabutylammonium fluoride solution in THF (2.04 mL, 2.04 mmol) and glacial acetic acid (0.2 mL, 3.33 mmol). Stop the reaction on the third day. Dilute with EtOAc and wash with saturated aqueous sodium bicarbonate solution and 0.1 N NaOH. Extract the aqueous layer three times with EtOAc. Combine the EtOAc fractions, dry (sodium sulfate), concentrate and purify (silica gel chromatography, eluting with 10:90 to 30:70 EtOAc:hexanes) to give the title compound (325 mg, 72%).

MS (ES): m/z=349.0 [M+H].

Preparation 34

7-Chloro-6-(3-phenylazetidin-1-yl)-3-(2,2,2-trifluoroacetyl)-2,3,4,5-tetrahydro-1H-benzo[d]azepine

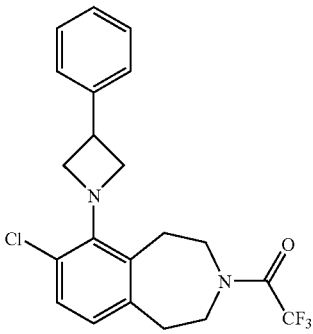

1-Benzhydryl-3-phenylazetidine

Under nitrogen mix copper (I) bromide (1.1 g, 7.6 mmol) and anhydrous THF (20 mL). Add a 3.0 M solution of phenylmagnesium bromide in ether slowly (2.5 mL, 7.6 mmol). Stir at RT for 90 min. Dissolve 1-(diphenylmethyl)-3-(methanesulphonyloxy)azetidine (2.0 g, 6.3 mmol) in anhydrous THF (10 mL) and transfer to the reaction mixture. Heat at 50° C. then stir at RT for 16 h. Dilute with EtOAc and wash with saturated aqueous sodium bicarbonate solution. Separate organic layer, dry (sodium sulfate), concentrate and purify (silica gel chromatography, eluting 10:90 EtOAc:hexanes) to give the title compound (515 mg, 27%).

MS (ES): m/z=300.1 [M+H].

3-Phenyl-azetidine

Add 20% palladium hydroxide on activated carbon (0.130 g) and ethanol (25 mL) to a Parr pressure vessel. Purge the reaction vessel with nitrogen, pressurize the reaction mixture with hydrogen (400 kPa), seal the vessel and agitate the mixture at RT for 15 min. Vent the hydrogen from the reaction vessel and purge the reaction vessel with nitrogen. Add 1-benzhydryl-3-phenylazetidine (0.515 g, 0.00172 mol) and ethanol (75 mL) to the pressure vessel. Purge the reaction vessel with nitrogen, pressurize the reaction mixture with hydrogen (400 kPa), seal the vessel and agitate the reaction at RT for 20 h. Turn off the agitation, vent the excess hydrogen from the vessel, purge the vessel with nitrogen and filter the reaction mixture to remove the palladium on carbon catalyst. Concentrate and purify (silica gel chromatography, eluting with 5:95 to 10:90 2 M ammonia in methanol:DCM) to give the title compound (76 mg, 34%).

MS (ES): m/z=134.1 [M+H].

7-Chloro-6-(3-phenylazetidin-1-yl)-3-(2,2,2-trifluoroacetyl)-2,3,4,5-tetrahydro-1H-benzo[d]azepine Use 7-chloro-3-(2,2,2-trifluoroacetyl)-6-trifluoromethanesulfonyloxy-2,3,4,5-tetrahydro-1H-benzo[d]azepine (prepared essentially as described in Preparation 1) (183 mg, 0.43 mmol), 3-phenylazetidine (75.2 mg, 0.56 mmol), palladium (II) acetate (9.0 mg, 0.04 mmol), tris (dibenzylideneacetone)dipalladium(0) (37 mg, 0.04 mmol), BINAP (racemic, 37 mg, 0.06 mmol), cesium carbonate (195 mg, 0.6 mmol), anhydrous toluene (10 mL) and degas and fill with nitrogen (3 times). Seal the system with septum and tighten it with copper wire when necessary. Heat the mixture at 95° C. for 8 h. Dilute with EtOAc, wash with saturated aqueous sodium bicarbonate solution, brine, dry (sodium sulfate), concentrate and purify (silica gel chromatography, eluting with 10:90 EtOAc:hexanes) to give the title compound (61 mg, 35%).

MS (ES): m/z=409.1 [M+H].

Preparation 35

6-(Azetidin-1-yl)-7-ethyl-3-(2,2,2-trifluoroacetyl)-2,3,4,5-tetrahydro-1H-benzo[d]azepine

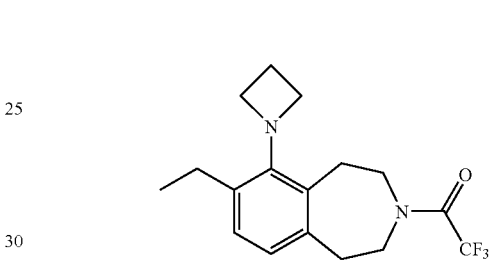

Use 7-ethyl-3-(2,2,2-trifluoroacetyl)-6-trifluoromethanesulfonyloxy-2,3,4,5-tetrahydro-1H-benzo[d]azepine (prepared essentially as described in Preparation 32) (335 mg, 0.80 mmol), trimethylene imine (228 mg, 4.0 mmol), palladium (II) acetate (18.0 mg, 0.08 mmol), BINAP (racemic, 74.7 mg, 0.12 mmol), cesium carbonate (391 mg, 1.2 mmol), anhydrous toluene (18 mL) and degas and fill with nitrogen (3 times). Seal the system with septum and tighten it with copper wire when necessary. Heat the mixture at 100° C. for 9 h. Dilute with EtOAc, wash with saturated aqueous sodium bicarbonate solution, brine, dry (sodium sulfate), concentrate and purify (silica gel chromatography, eluting with 10:90 EtOAc:hexanes) to give the title compound (185 mg, 71%).

MS (ES): m/z=327.1 [M+H].

Preparation 36

3-(2,2,2-Trifluoroacetyl)-6-trifluoromethane-sulfonyloxy-2,3,4,5-tetrahydro-1H-benzo[d]azepine

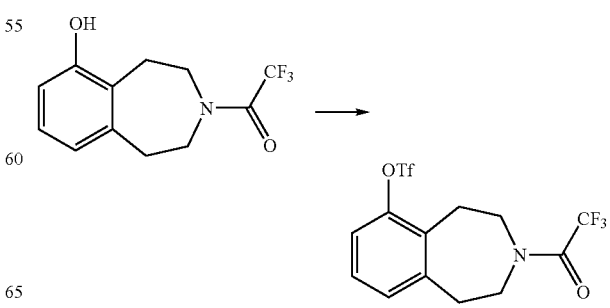

Cool a solution of 6-hydroxy-3-(2,2,2-trifluoroacetyl)-2,3, 4,5-tetrahydro-1H-benzo[d]azepine (prepared essentially as described in Preparation 1) (2 g, 7.72 mmol), triethylamine (1.4 mL, 10.1 mmol) and DCM (50 mL) in a cryogenic bath set at −30° C. and add dropwise trifluoromethanesulfonic anhydride (1.7 mL, 10.1 mmol) over 20 min. Stir at −30° C. for 2 h and then warm to RT overnight. Wash the reaction mixture sequentially with water (100 mL), 1 N HCl (100 mL), water (200 mL), and brine (200 mL). Dry (sodium sulfate) and concentrate to give the title compound as a colorless to light yellow oil (2.7 g, 89%) that was used without purification. Obtain an analytical sample utilizing silica gel chromatography eluting with 90:10 hexanes:EtOAc to give the title compound as an off-white waxy solid.

GC-MS: m/z=391 [M+]

Preparation 37

2-(3-Chloropropyl)-2-thiophen-2-yl[1,3]dioxolane

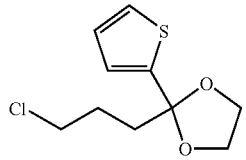

Add 4-chloro-1-thiophen-2-yl-butan-1-one (10 g, 53 mmol), ethylene glycol (8.14 g, 131.2 mmol) and p-toluene sulfonic acid (362 mg, 1.6 mmol) to benzene (150 mL) and heat at reflux for 16 h under a water trap. Cool the reaction to RT and wash with 1 N NaOH solution (100 mL) and brine (150 mL). Dry (sodium sulfate) and concentrate to give the title product as a dark oil (12 g, 97%).

MS (EI): m/z=232.7 [M+], $^1$H NMR (300 MHz, CDCl$_3$) δ 7.24 (m, 1H), 7.01 (m, 1H), 3.9 (m, 4H), 3.55 (t, J=6.6 Hz, 2H), 2.15 (m, 2H), 1.91 (m, 2H).

Preparation 38

(+/−)-7-Chloro-3-(2,2,2-trifluoroacetyl)-6-(2-phenyl-pyrrolidin-1-yl)-2,3,4,5-tetrahydro-1H-benzo[d]azepine

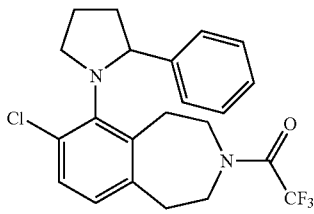

2-(3-Chloropropyl)-2-phenyl-[1,3]dioxolane

Add 4-chlorobutyrophenone (50 g, 274 mmol), ethylene glycol (28 g, 452 mmol) and p-toluenesulfonic acid (1.04 g, 5.48 mmol) to benzene (600 mL) and heat at reflux for 16 h under a water trap. Cool the reaction to RT and wash with 1 N NaOH (500 mL) and brine (750 mL). Dry (sodium sulfate) and concentrate to give a solid. Recrystallize the solid from hot hexanes to give the title compound as a white powder (38 g, 61%).

MS (EI): m/z=226.7 [M+].

2-[3-(2-Phenyl-[1,3]dioxolan-2-yl)-propyl]-isoindole-1,3-dione

Add 2-(3-chloropropyl)-2-phenyl-[1,3]dioxolane (38 g, 168 mmol) and potassium phthalimide (34.2 g, 184.4 mmol) to DMF (80 mL) and stir for 40 min at 150° C. Cool the reaction to RT, dilute with water (1 L) and extract the mixture with a mixture of EtOAc (500 mL) and hexanes (500 mL) and DCM (2 L). Dry (sodium sulfate), concentrate and recrystallize the solid from hot ethanol (600 mL). Filter and dry the residue under vacuum to isolate the title compound as a white solid (47.62 g, 84%).

MS (EI): m/z=337.1 [M+].

3-(2-Phenyl-[1,3]dioxolan-2-yl)-propylamine

Dissolve 2-[3-(2-phenyl-[1,3]dioxolan-2-yl)-propyl]-isoindole-1,3-dione (38 g, 112.91 mmol) in 2 M methylamine solution in methanol (300 mL) and heat in a sealed tube for 3 h at 50° C. Cool the solution to RT, concentrate and purify (silica gel chromatography, eluting with 25:75 DCM:2 M ammonia in methanol) to give the title compound as an oil (11 g, 47%).

MS (ES): m/z=208.1 [M+H].

7-Chloro-3-(2,2,2-trifluoroacetyl)-6-[3-(2-phenyl-[1,3]-dioxolan-2-yl)-propylamino]-2,3,4,5-tetrahydro-1H-benzo[d]azepine Place 7-chloro-3-(2,2,2-trifluoroacetyl)-6-trifluoromethanesulfonyloxy-2,3,4,5-tetrahydro-1H-benzo[d]azepine (5 g, 11.7 mmol) in toluene (100 mL) with 3-(2-phenyl-[1,3]dioxolan-2-yl)-propylamine (4.85 g, 23.4 mmol), tris(dibenzylideneacetone)dipalladium (0) (1.1 g, 1.17 mmol), racemic 2,2'-bis(diphenylphosphino)-1,1'-binapthyl (5.1 g, 8.19 mmol), palladium acetate (525 mg, 2.34 mmol) and cesium carbonate (5.34 g, 16.38 mmol). Heat for 16 h at 95° C. in a sealed tube. Cool the reaction to RT, dilute with EtOAc (600 mL) and filter. Concentrate the filtrate and chromatograph on silica gel, eluting with 10:90 to 25:75 EtOAc:hexanes to give the title compound contaminated with some colored impurities. Dissolve the residue in 20:80 EtOAc:hexanes (100 mL) and filter to remove solids. Chromatograph the filtrate on silica gel, eluting with 10:90 EtOAc:hexanes to give the title compound as an orange oil (4.32 g, 76%).

MS (ES): m/z=483.2 [M+H].

(+/−)-7-Chloro-3-(2,2,2-trifluoroacetyl)-6-(2-phenyl-pyrrolidin-1-yl)-2,3,4,5-tetrahydro-1H-benzo[d]azepine Dissolve 7-chloro-3-(2,2,2-trifluoroacetyl)-6-[3-(2-phenyl-[1,3]dioxolan-2-yl)-propylamino]-2,3,4,5-tetrahydro-1H-benzo[d]azepine (2.78 g, 5.76 mmol) in DCM (25 mL) and add methanol (1 mL) and 2 N HCl in diethyl ether (25 mL) and stir at RT for 16 h. Concentrate and dissolve the residue in acetic acid (30 mL) and add sodium cyanoborohydride (1.81 g, 28.78 mmol). Stir the reaction at RT for 1 h then concentrate. Dissolve the residue in EtOAc (500 mL) and extract with saturated sodium bicarbonate solution (500 mL). Extract the aqueous layer with EtOAc (100 mL) and combine the organic fractions, dry (sodium sulfate), concentrate and purify (silica gel chromatography, eluting with 10:90 EtOAc:hexanes) to give the title compound as a foam (1.72 g, 71%).

MS (ES): m/z=423.1 [M+H].

The compounds of Preparations 39-42 may be prepared essentially as described in Preparation 38 by using the appropriately substituted [1,3]dioxolane available either commercially or prepared essentially as described in J. Med. Chem., 34 (1), 12-19 (1991).

| Prep | Compound Structure | Compound Name | MS (ES) [M + H] |
|---|---|---|---|
| 39 | 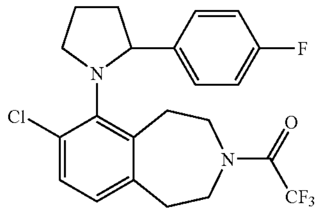 | (+/−)-7-Chloro-3-(2,2,2-trifluoroacetyl)-6-[2-(4-fluorophenyl)-pyrrolidin-1-yl]-2,3,4,5-tetrahydro-1H-benzo[d]azepine | 441.1 |
| 40 | 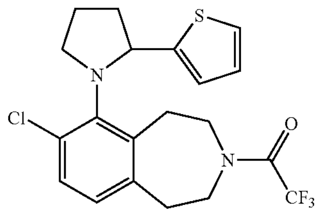 | (+/−)-7-Chloro-3-(2,2,2-trifluoroacetyl)-6-(2-thiophen-2-yl-pyrrolidin-1-yl)-2,3,4,5-tetrahydro-1H-benzo[d]azepine | 429.1 |

Preparation 43

(+/−)-7-Chloro-3-benzoxycarbonyl-6-(2-methylpyrrolidin-1-yl)-2,3,4,5-tetrahydro-1H-benzo[d]azepine

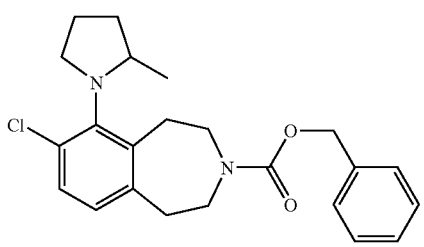

(+/−)-7-Chloro-3-(2,2,2-trifluoroacetyl)-6-(2-methyl-pyrrolidin-1-yl)-2,3,4,5-tetrahydro-1H-benzo[d]azepine Place 7-chloro-3-(2,2,2-trifluoroacetyl)-6-trifluoromethanesulfonyloxy-2,3,4,5-tetrahydro-1H-benzo[d]azepine (prepared essentially as described in Preparation 1) (3 g, 7.08 mmol) in toluene (60 mL) with 3-(2-methyl-[1,3]dioxolan-2-yl)-propylamine (prepared essentially as described in Preparation 38) (3.08 g, 21.24 mmol), tris(dibenzylideneacetone)dipalladium (1.3 g, 1.42 mmol), racemic 2,2'-bis(diphenylphosphino)-1,1'-binapthyl (1.77 g, 2.84 mmol), and cesium carbonate (3.3 g, 9.91 mmol) and heat for 16 h at 95° C. in a sealed tube. Cool the reaction to RT, dilute with EtOAc (600 mL) and filter. Concentrate the filtrate and purify (silica gel chromatography, eluting with 10:90 to 25:75 EtOAc:hexanes) to give the crude product as an orange oil (1.72 g). Dissolve 7-chloro-3-(2,2,2-trifluoroacetyl)-6-[3-(2-methyl[1,3]dioxolan-2-yl)-propylamino]-2,3,4,5-tetrahydro-1H-benzo[d]azepine (1.72 g, 4.09 mmol) in DCM (20 mL) and add methanol (2 mL) and 2 N HCl in diethyl ether (20 mL) and stir at RT for 3 h. Concentrate and dissolve the residue in acetic acid (30 mL) and add sodium cyanoborohydride (1.28 g, 20.43 mmol). Stir the reaction at RT for 0.5 h then concentrate to remove the acetic acid. Dissolve the residue in DCM (200 mL) and extract with saturated aqueous sodium bicarbonate solution (400 mL), Extract the aqueous layer with DCM (100 mL) and combine the organic fractions, dry (sodium sulfate), concentrate and purify (silica gel chromatography, eluting with 10:90 EtOAc:hexanes) to give the title compound as a foam (1.2 g, 81%).

MS (ES): m/z=361.1 [M+H].

(+/−)-7-Chloro-3-benzyloxycarbonyl-6-(2-methylpyrrolidin-1-yl)-2,3,4,5-tetrahydro-1H-benzo[d]azepine Dissolve (+/−)-7-chloro-3-(2,2,2-trifluoroacetyl)-6-(2-methyl-pyrrolidin-1-yl)-2,3,4,5-tetrahydro-1H-benzo[d]azepine (1 g, 2.77 mmol) in a mixture of methanol and 2 N NaOH solution (65 mL of 4:1) and stir at RT for 1 h. Concentrate to remove methanol and extract the mixture between DCM and water (300 mL of each). Dry (sodium sulfate) and concentrate to an oil. Dissolve the oil in DCM (200 mL) and add dimethylaminopyridine (20 mg), and dibenzyl dicarbonate (873 mg, 3.05 mmol) and stir at RT for 3 h. Concentrate the reaction and purify (silica gel chromatography, eluting with 5:95 to 15:85 EtOAc:hexanes) to give the title compound as a clear oil (775 mg, 70%).

MS (ES): m/z=399.2 [M+H].

EXAMPLE 1

7-Chloro-6-(3,5-dimethylpyrazol-1-yl)-2,3,4,5-tetrahydro-1H-benzo[d]azepine succinate

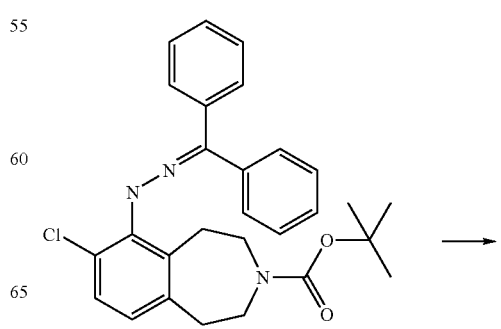

-continued

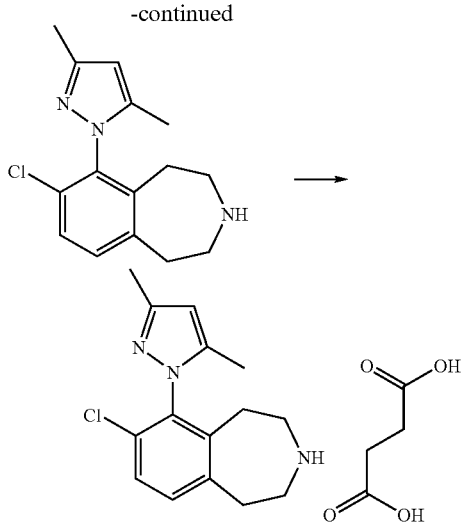

7-Chloro-6-(3,5-dimethyl-pyrazol-1-yl)-2,3,4,5-tetrahydro-1H-benzo[d]azepine Dissolve 3-tert-butoxycarbonyl-7-chloro-6-(N-benzhydrylidene-hydrazino)-2,3,4,5-tetrahydro-1H-benzo[d]azepine (prepared essentially as described in Preparation 2) (380 mg, 0.8 mmol) in ethanol (1 mL) under nitrogen and add 2,4-pentanedione (125 μL, 1.2 mmol) and 10 N HCl (2 mL). Stir at reflux overnight, concentrate and purify (SCX2®, followed by chromatography by UV Flex) to give the title compound (130.56 mg, 60%).

MS (ES): m/z=276 [M+H].

7-Chloro-6-(3,5-dimethylpyrazol-1-yl)-2,3,4,5-tetrahydro-1H-benzo[d]azepine succinate Add succinic acid (55.9 mg, 0.47 mmol) to a solution of 7-chloro-6-(3,5-dimethylpyrazol-1-yl)-2,3,4,5-tetrahydro-1H-benzo[d]azepine (130.5 mg, 0.47 mmol) in methanol (3 mL). Stir the reaction at RT for 15 min, and concentrate to give the title compound (145.19 mg, 78%).

MS (ES): m/z=276 [M+H].

EXAMPLES 2-16

The compounds of Examples 2-16 may be prepared essentially as described in Example 1 by using the appropriately substituted 2,4-pentanedione. The regioisomers are separated using UV Flex purification, preparative LCMS or HPLC. The concentrates are lyophilized to provided the final products.

| Ex | Compound Structure | Compound Name | MS (ES) [M + H] |
|----|--------------------|---------------|-----------------|
| 2 | 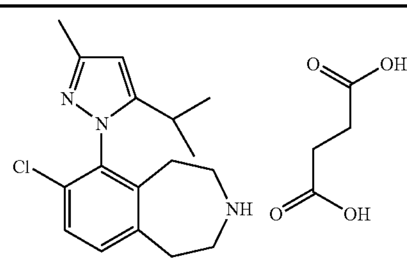 | 7-Chloro-6-(5-isopropyl-3-methyl-pyrazol-1-yl)-2,3,4,5-tetrahydro-1H-benzo[d]azepine succinate | 304 |
| 3 | 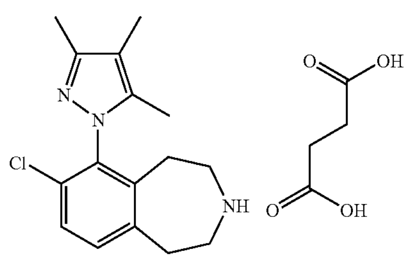 | 7-Chloro-6-(3,4,5-trimethyl-pyrazol-1-yl)-2,3,4,5-tetrahydro-1H-benzo[d]azepine succinate | 290 |
| 4 | 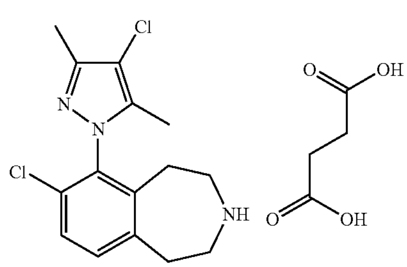 | 7-Chloro-6-(4-chloro-3,5-dimethyl-pyrazol-1-yl)-2,3,4,5-tetrahydro-1H-benzo[d]azepine succinate | 310 |

| Ex | Compound Structure | Compound Name | MS (ES) [M + H] |
|---|---|---|---|
| 5 | 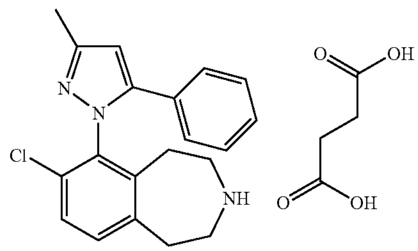 | 7-Chloro-6-(3-methyl-5-phenyl-pyrazol-1-yl)-2,3,4,5-tetrahydro-1H-benzo[d]azepine succinate | 338 |
| 6 | 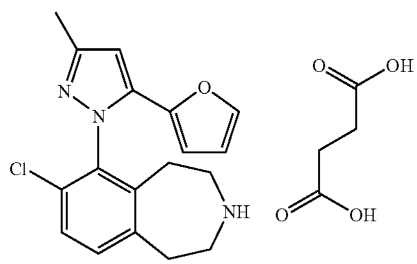 | 7-Chloro-6-(5-furan-2-yl-3-methyl-pyrazol-1-yl)-2,3,4,5-tetrahydro-1H-benzo[d]azepine succinate | 328 |
| 7 | 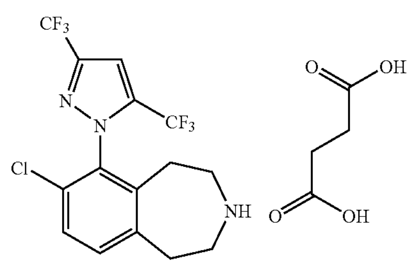 | 6-(3,5-Bistrifluoromethyl-pyrazol-1-yl)-7-chloro-2,3,4,5-tetrahydro-1H-benzo[d]azepine succinate | 384 |
| 8 | 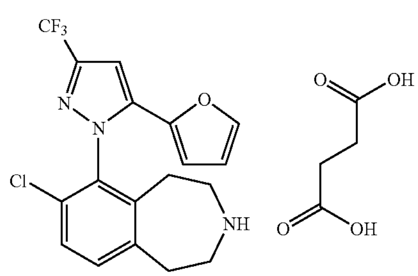 | 7-Chloro-6-(5-furan-2-yl-3-trifluoromethyl-pyrazol-1-yl)-2,3,4,5-tetrahydro-1H-benzo[d]azepine succinate | 382 |
| 9 | 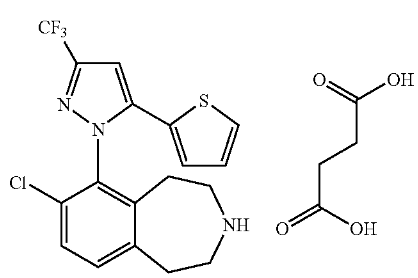 | 7-Chloro-6-(5-thiophen-2-yl-3-trifluoromethyl-pyrazol-1-yl)-2,3,4,5-tetrahydro-1H-benzo[d]azepine succinate | 398 |

-continued

| Ex | Compound Structure | Compound Name | MS (ES) [M + H] |
|---|---|---|---|
| 10 | 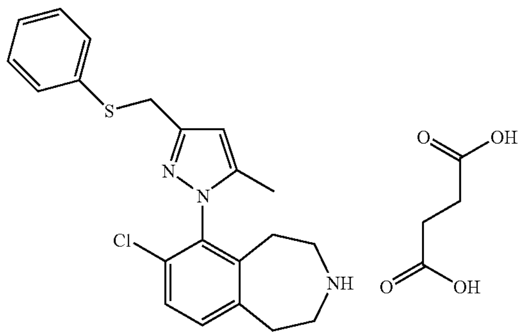 | 7-Chloro-6-(5-methyl-3-phenylthiomethyl-pyrazol-1-yl)-2,3,4,5-tetrahydro-1H-benzo[d]azepine succinate | 384 |
| 11 | 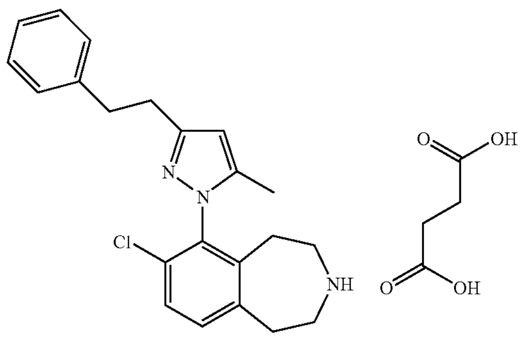 | 7-Chloro-6-(5-methyl-3-phenethyl-pyrazol-1-yl)-2,3,4,5-tetrahydro-1H-benzo[d]azepine succinate | 366 |
| 12 | 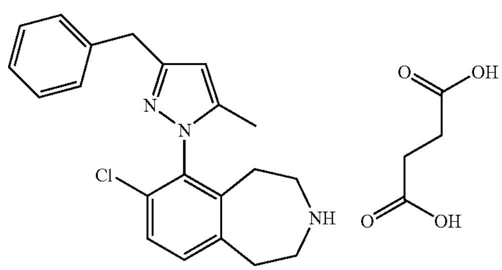 | 6-(3-Benzyl-5-methyl-pyrazol-1-yl)-7-chloro-2,3,4,5-tetrahydro-1H-benzo[d]azepine succinate | 352 |
| 13 | 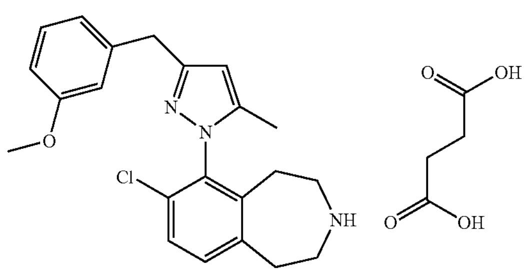 | 7-Chloro-6-[3-(3-methoxybenzyl)-5-methyl-pyrazol-1-yl]-2,3,4,5-tetrahydro-1H-benzo[d]azepine succinate | 382 |
| 14 | 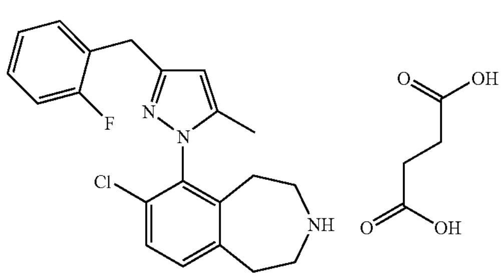 | 7-Chloro-6-[3-(2-fluorobenzyl)-5-methyl-pyrazol-1-yl]-2,3,4,5-tetrahydro-1H-benzo[d]azepine succinate | 370 |

| Ex | Compound Structure | Compound Name | MS (ES) [M + H] |
|---|---|---|---|
| 15 | 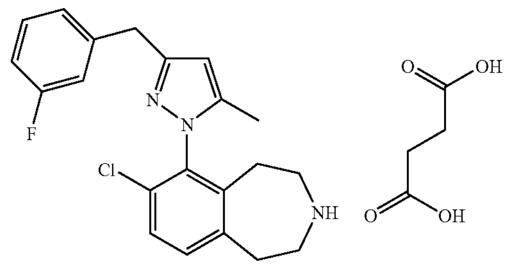 | 7-Chloro-6-[3-(3-fluorobenzyl)-5-methyl-pyrazol-1-yl]-2,3,4,5-tetrahydro-1H-benzo[d]azepine succinate | 370 |
| 16 | 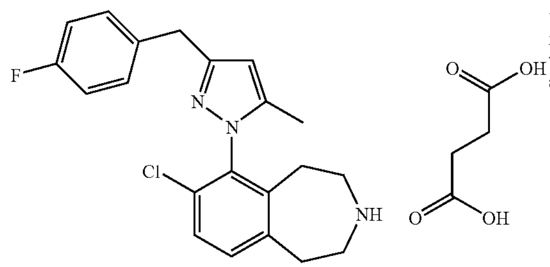 | 7-Chloro-6-[3-(4-fluorobenzyl)-5-methyl-pyrazol-1-yl]-2,3,4,5-tetrahydro-1H-benzo[d]azepine succinate | 370 |

EXAMPLE 17

7-Chloro-6-(5-pyridin-2-yl-pyrazol-1-yl)-2,3,4,5-tetrahydro-1H-benzo[d]azepine succinate

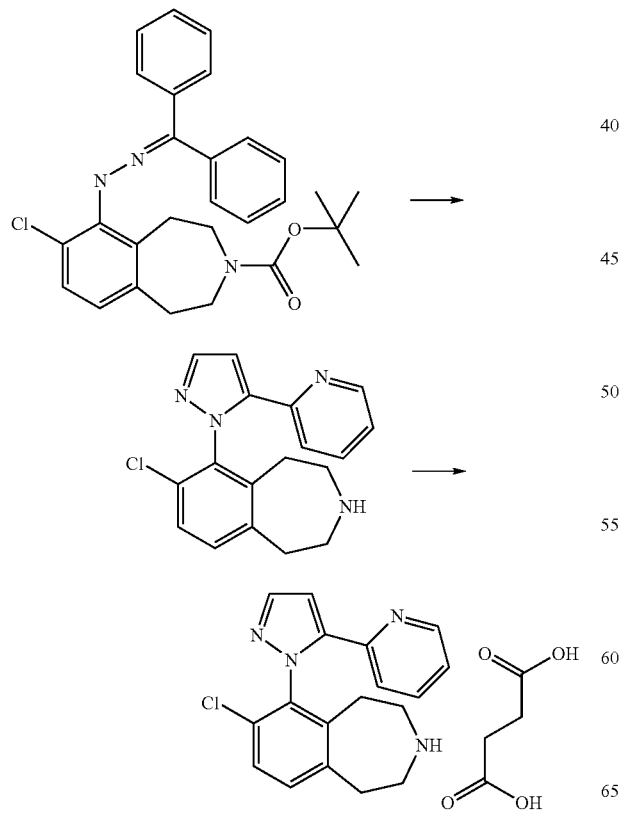

7-Chloro-6-(5-pyridin-2-yl-pyrazol-1-yl)-2,3,4,5-tetrahydro-1H-benzo[d]azepine Stir together 3-tert-butoxycarbonyl-7-chloro-6-(N'-benzhydrylidene-hydrazino)-2,3,4,5-tetrahydro-1H-benzo[d]azepine (prepared essentially as described in Preparation 2) (150 mg, 0.32 mmol), (2E)-3-(dimethylamino)-1-(2-pyridyl)prop-2-en-1-one (see preparation 17) (111 mg, 0.64 mmol) and concentrated HCl (1 mL) in ethanol (5 mL) at reflux for 17 h under nitrogen. Concentrate, purify (SCX2®, then silica gel chromatography, eluting with 95:5 to 90:10 DCM:methanol with 2 M ammonia) and separate the regioisomers by Flex (Supelco Discovery C18 column, 21.2×100 mm, 5 μm packing, eluting at 20 mL/min with water/acetonitrile/acetic acid gradient over 15 min at 220 and 254 nm), and further purify with an SCX2® column to give the title compound (11 mg, 11%).

MS (ES): m/z=325 [M+H].

7-Chloro-6-(5-pyridin-2-yl-pyrazol-1-yl)-2,3,4,5-tetrahydro-1H-benzo[d]azepine succinate Add a solution of succinic acid (4 mg, 0.034 mmol) in methanol (3 mL) to 7-chloro-6-(5-pyridin-2-yl-pyrazol-1-yl)-2,3,4,5-tetrahydro-1H-benzo[d]azepine (11 mg, 0.034 mmol). Stir the reaction at RT for 5 min, then concentrate and lyophilize to give the title compound (15 mg, 100%).

MS (ES): m/z=325 [M+H].

EXAMPLES 18-33

Examples 18-33 may be prepared essentially as described in Example 17 by using the appropriately substituted (2E)-3-(dimethylamino)prop-2-en-1-one. Separate regioisomers using UV Flex purification, preparative LCMS or HPLC.

| Ex | Compound Structure | Compound Name | MS (ES) [M + H] |
|---|---|---|---|
| 18 | 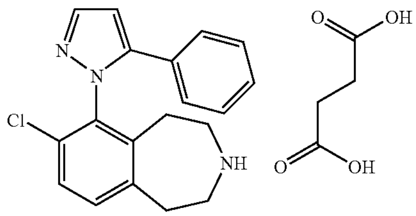 | 7-Chloro-6-(5-phenyl-pyrazol-1-yl)-2,3,4,5-tetrahydro-1H-benzo[d]azepine succinate | 324 |
| 19 | 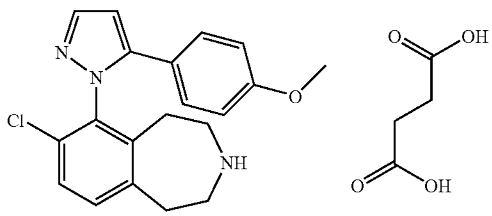 | 7-Chloro-6-[5-(4-methoxyphenyl)-pyrazol-1-yl]-2,3,4,5-tetrahydro-1H-benzo[d]azepine succinate | 354 |
| 20 | 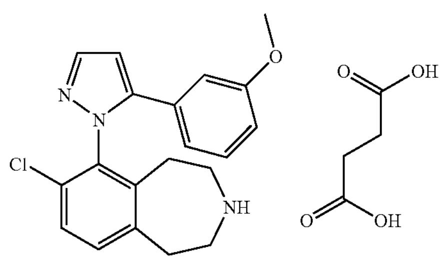 | 7-Chloro-6-[5-(3-methoxyphenyl)-pyrazol-1-yl]-2,3,4,5-tetrahydro-1H-benzo[d]azepine succinate | 354 |
| 21 | 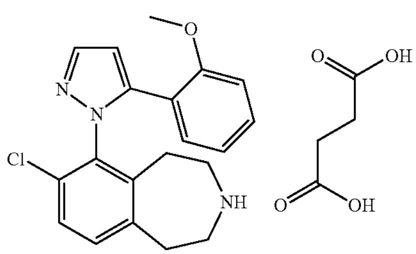 | 7-Chloro-6-[5-(2-methoxyphenyl)-pyrazol-1-yl]-2,3,4,5-tetrahydro-1H-benzo[d]azepine succinate | 354 |
| 22 | 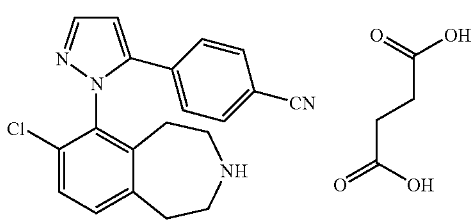 | 7-Chloro-6-[5-(4-cyanophenyl)-pyrazol-1-yl]-2,3,4,5-tetrahydro-1H-benzo[d]azepine succinate | 349 |
| 23 | 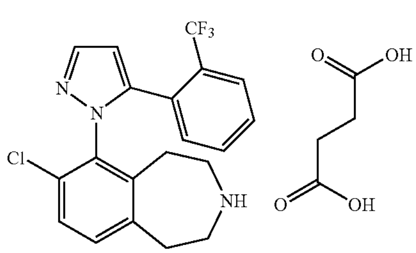 | 7-Chloro-6-[5-(2-trifluoromethyl-phenyl)-pyrazol-1-yl]-2,3,4,5-tetrahydro-1H-benzo[d]azepine succinate | 392 |

| Ex | Compound Structure | Compound Name | MS (ES) [M + H] |
|---|---|---|---|
| 24 | 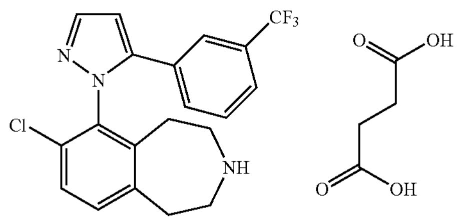 | 7-Chloro-6-[5-(3-trifluoromethyl-phenyl)-pyrazol-1-yl]-2,3,4,5-tetrahydro-1H-benzo[d]azepine succinate | 392 |
| 25 | 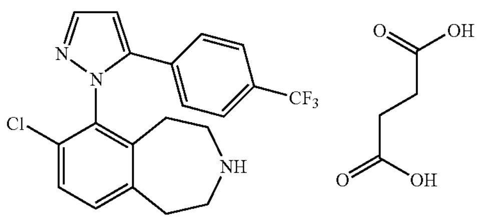 | 7-Chloro-6-[5-(4-trifluoromethyl-phenyl)-pyrazol-1-yl]-2,3,4,5-tetrahydro-1H-benzo[d]azepine succinate | 392 |
| 26 | 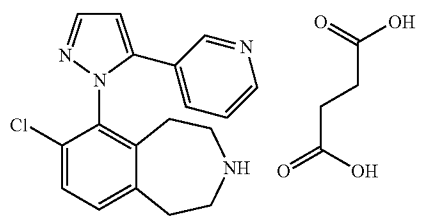 | 7-Chloro-6-(5-pyridin-3-yl-pyrazol-1-yl)-2,3,4,5-tetrahydro-1H-benzo[d]azepine succinate | 325 |
| 27 | 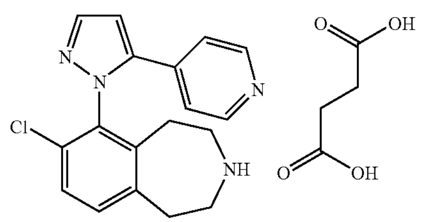 | 7-Chloro-6-(5-pyridin-4-yl-pyrazol-1-yl)-2,3,4,5-tetrahydro-1H-benzo[d]azepine succinate | 325 |
| 28 | 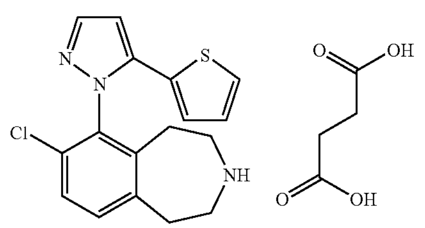 | 7-Chloro-6-(5-thiophen-2-yl-pyrazol-1-yl)-2,3,4,5-tetrahydro-1H-benzo[d]azepine succinate | 330 |
| 29 | 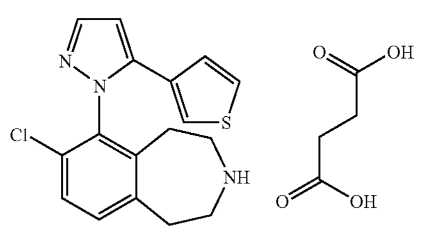 | 7-Chloro-6-(5-thiophen-3-yl-pyrazol-1-yl)-2,3,4,5-tetrahydro-1H-benzo[d]azepine succinate | 330 |
| 30 | 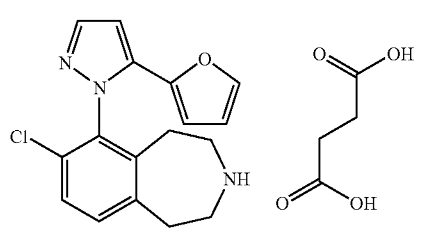 | 7-Chloro-6-(5-furan-2-yl-pyrazol-1-yl)-2,3,4,5-tetrahydro-1H-benzo[d]azepine succinate | 314 |

| Ex | Compound Structure | Compound Name | MS (ES) [M + H] |
|---|---|---|---|
| 31 | 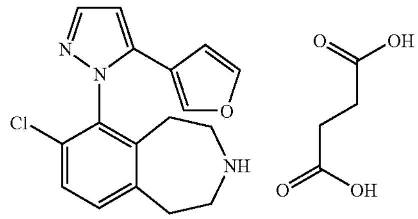 | 7-Chloro-6-(5-furan-3-yl-pyrazol-1-yl)-2,3,4,5-tetrahydro-1H-benzo[d]azepine succinate | 314 |
| 32 | 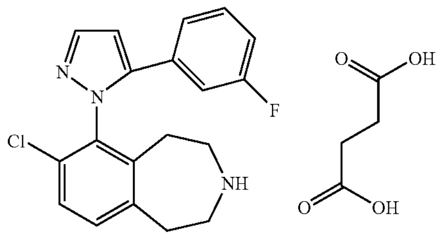 | 6-[5-(3-fluorophenyl)-pyrazol-1-yl]-7-chloro-2,3,4,5-tetrahydro-1H-benzo[d]azepine succinate | 342 |
| 33 | 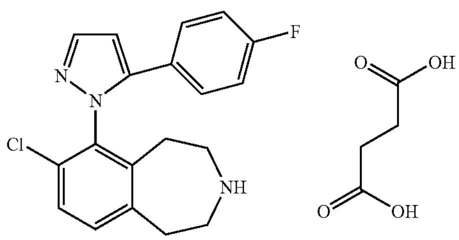 | 6-[5-(4-fluorophenyl)-pyrazol-1-yl]-7-chloro-2,3,4,5-tetrahydro-1H-benzo[d]azepine succinate | 342 |

EXAMPLE 34

6-(Azetidin-1-yl)-7-chloro-2,3,4,5-tetrahydro-1H-benzo[d]azepine succinate

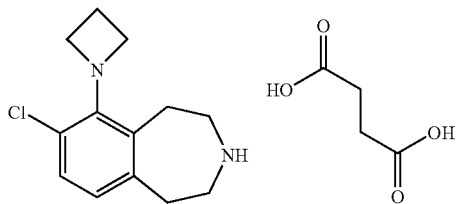

6-(Azetidin-1-yl)-7-chloro-3-(2,2,2-trifluoroacetyl)-, 2,3,4,5-tetrahydro-1H-benzo[d]azepine Add 7-chloro-3-(2,2,2-trifluoroacetyl)-6-trifluoromethanesulfonyloxy-2,3,4,5-tetrahydro-1H-benzo[d] azepine (1.500 g, 3.52 mmol), palladium acetate (78.6 mg, 0.35 mmol), BINAP (342 mg, 0.55 mmol), cesium carbonate (1.70 g, 5.28 mmol) and anhydrous toluene in a flask with septum, degas and refill the flask with nitrogen. Add azetidine (1.005 g, 17.6 mmol) and heat the reaction mixture in the sealed flask at 100° C. with stirring overnight. Cool the reaction to RT, filter, concentrate and purify (silica gel chromatography, eluting with 1:6 EtOAc:hexanes) to give the title compound as an oil (453 mg, 38.8%).

MS (ES): m/z=333.0 [M+H], $^1$H NMR (300 MHz, CDCl$_3$) δ 7.07 (dd, 1H), 6.70 (dd, 1H), 4.16 (m, 4H), 3.74 (m, 2H), 3.66 (m, 2H), 3.18 (m, 1H), 3.10 (m, 1H), 2.91 (m, 2H), 2.30 (m, 2H).

6-(Azetidin-1-yl)-7-chloro-2,3,4,5-tetrahydro-1H-benzo[d]azepine

Dissolve 6-(azetidin-1-yl)-7-chloro-3-(2,2,2-trifluoroacetyl)-,2,3,4,5-tetrahydro-1H-benzo[d]azepine (112 mg, 0.34 mmol) in methanol (10 mL) and add 7 N ammonia in methanol (10 mL) and stir for 2 h. Concentrate and purify (silica gel chromatography, eluting with 7:93 2 M ammonia in methanol:DCM to give the free amine of the title compound as an oil (63 mg, 78.9%).

MS (ES): m/z=237.0 [M+H], $^1$H NMR (300 MHz, CDCl$_3$) δ 7.01 (d, 1H), 6.65 (d, 1H), 4.19 (t, 4H), 3.04 (m, 2H), 2.96 (m, 4H), 2.86 (m, 2H), 2.25 (pent, 2H), 1.84 (br s, 1H).

6-(Azetidin-1-yl)-7-chloro-2,3,4,5-tetrahydro-1H-benzo[d]azepine succinate

Dissolve 6-(azetidin-1-yl)-7-chloro-2,3,4,5-tetrahydro-1H-benzo[d]azepine (63 mg, 0.27 mmol) in methanol (1 mL). Add one equivalent of succinic acid (31 mg, 0.27 mmol) in methanol (1 mL) stir, concentrate to an oil, add anhydrous diethyl ether to precipitate out the solid. Decant the solvent and dry the solid under a stream of nitrogen to give the title compound as a solid.

MS (ES): m/z=237.3 [M+H].

EXAMPLES 35-39

The compounds of Examples 35-39 may be prepared essentially as described in Example 34 by using the appropriate cyclic amine.

| EX | Compound Structure | Compound Name | MS (ES) [M + H] |
|---|---|---|---|
| 35 | 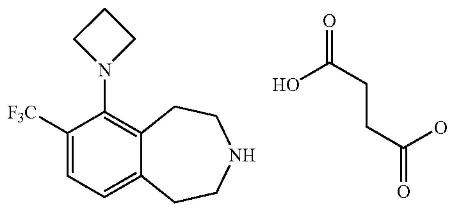 | 6-(Azetidin-1-yl)-7-trifluoromethyl-2,3,4,5-tetrahydro-1H-benzo[d]azepine succinate | 271.0 |
| 36 | 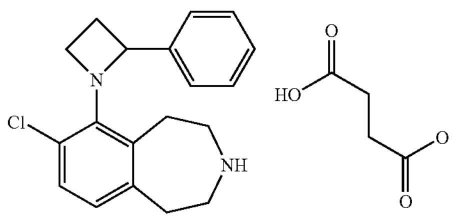 | (+/−)-7-Chloro-6-(2-phenylazetidin-1-yl)-2,3,4,5-tetrahydro-1H-benzo[d]azepine succinate | 313.1 |
| 37 | 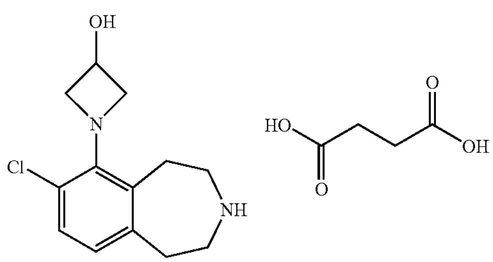 | 7-Chloro-6-(3-hydroxy-azetidin-1-yl)-2,3,4,5-tetrahydro-1H-benzo[d]azepine succinate | 253.2 |
| 38 | 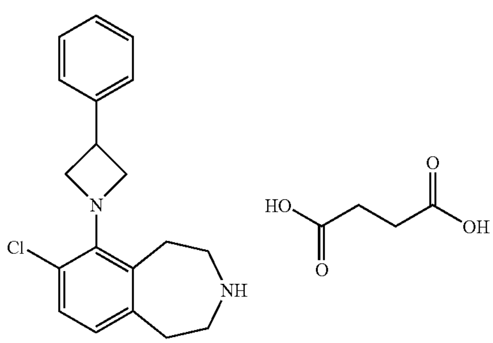 | 7-Chloro-6-(3-phenyl-azetidin-1-yl)-2,3,4,5-tetrahydro-1H-benzo[d]azepine succinate | 313.2 |
| 39 | 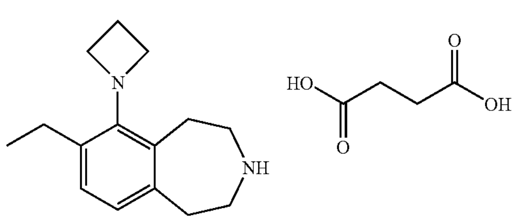 | 6-(Azetidin-1-yl)-7-ethyl-2,3,4,5-tetrahydro-1H-benzo[d]azepine succinate | 231.3 |

EXAMPLE 40

7-Chloro-6-(3,3-dimethyl-azetidin-1-yl)-2,3,4,5-tetrahydro-1H-benzo[d]azepine succinate

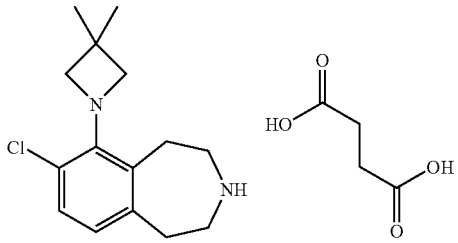

Dissolve 7-chloro-6-(3-hydroxy-2,2-dimethyl-propylamino)-3-(2,2,2-trifluoroacetyl)-2,3,4,5-tetrahydro-1H-benzo[d]azepine (prepared as described in Preparation 30) (250 mg, 0.66 mmol) in DCM (30 mL). Add diethyl azodicarboxylate (150 mg, 0.86 mmol), and triphenylphosphine (226 mg, 0.86 mmol) and stir at 40° C. for 16 h. Quench with saturated aqueous sodium bicarbonate solution, extract with DCM three times. Combine the organic layers, dry (sodium sulfate), concentrate and purify (silica gel chromatography, eluting with 1:8 EtOAc:hexanes) to provide 7-chloro-6-(3,3-dimethylazetidin-1-yl)-3-(2,2,2-trifluoroacetyl)-2,3,4,5-tetrahydro-1H-benzo[d]azepine (175 mg, 74%). MS (ES) m/z:=361.2 [M+H]. Deprotection and the succinate salt formation of the free amine is achieved essentially as described in Example 34 to give the title compound (91 mg, 71%).

MS (ES+) m/z: 265.1 [M+H].

EXAMPLE 41

(+/−)-6-(2-Phenylpyrrolidin-1-yl)-2,3,4,5-tetrahydro-1H-benzo[d]azepine succinate

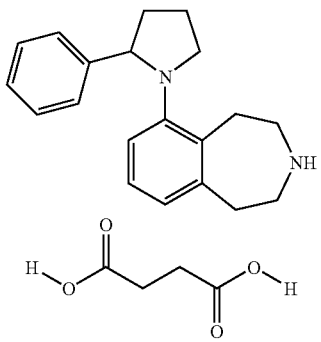

Add 3-(2,2,2-trifluoroacetyl)-6-trifluoromethanesulfonyloxy-2,3,4,5-tetrahydro-1H-benzo[d]azepine (prepared essentially as described in Preparation 36) (500 mg, 1.28 mmol), 2-phenyl-pyrrolidine (227 mg, 1.54 mmol), palladium acetate (29 mg, 0.128 mmol), racemic 2,2'-bis(diphenylphosphino)-1,1'-binapthyl (239 mg, 0.384 mmol) and cesium carbonate (584 mg, 1.79 mmol) to toluene (5 mL) and stir for 16 h at 95° C. Cool the reaction to RT, and dilute with EtOAc (60 mL). Filter the slurry and concentrate the filtrate. Chromatograph the residue on silica gel, eluting with 0:100-15:85 EtOAc:hexanes to give the crude product (220 mg, 44%) as a yellow oil. Dissolve the crude residue in 4 M HCl in dioxane (10 mL) and stir the reaction at RT for 1 h. Concentrate the reaction and subject the residue to SCX ion exchange chromatography to give 160 mg of freebase material. Dissolve the residue in methanol (5 mL) and add succinic acid (1 eq.) concentrate the solution, slurry in diethyl ether, filter and dry the residue under vacuum to isolate the title compound as an off white solid (160 mg, 30%).

MS (ES): m/z=293.1 [M+H].

EXAMPLES 42 AND 43

(+ and −)-7-Chloro-6-(2-phenyl-pyrrolidin-1-yl)-2,3,4,5-tetrahydro-1H-benzo[d]azepine succinate

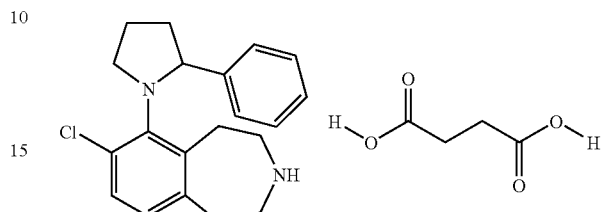

(−)-7-Chloro-6-(2-phenyl-pyrrolidin-1-yl)-2,3,4,5-tetrahydro-1H-benzo[d]azepine succinate
(Example 42)

Separate the enantiomers of the (+/−)-7-chloro-3-(2,2,2-trifluoroacetyl)-6-(2-phenyl-pyrrolidin-1-yl)-2,3,4,5-tetrahydro-1H-benzo[d]azepine mixture (prepared essentially as described in Preparation 38) via chiral normal phase chromatography (Chiralcel OD column, eluting with 97:3 heptane:isopropanol with 0.2% dimethylethyl amine) to give two enantiomers. Take the second eluting enantiomer (3.57 g, 8.44 mmol) and dissolve in methanol (60 mL) and add 2 N sodium hydroxide solution (10 mL) and stir at RT for 1 h. Concentrate the reaction to remove methanol and extract the material between water and DCM (300 mL each) and back extract the water with DCM (100 mL). Dry (sodium sulfate), concentrate and purify (silica gel chromatography, eluting with 15:85 DCM:2 M ammonia in methanol) to give the title compound as the freebase. Dissolve the material in methanol and add succinic acid (1 equivalent) and stir until a solution results. Concentrate the reaction to a solid, triturate the solid with ether, and filter. Dry the solid under vacuum at 50° C. for 16 h. to give the title compound (3.18 g, 85%) as a white solid.

MS (ES): m/z=327.2 [M+H], $[\alpha]_D$=−43.4° (c=0.5, MeOH).

(+)-7-Chloro-6-(2-phenyl-pyrrolidin-1-yl)-2,3,45-tetrahydro-1H-benzo[d]azepine succinate
(Example 43)

Separate the enantiomers of the (+/−)-7-chloro-3-(2,2,2-trifluoroacetyl)-6-(2-phenyl-pyrrolidin-1-yl)-2,3,4,5-tetrahydro-1H-benzo[d]azepine mixture via chiral normal phase chromatography (Chiralcel OD column, eluting with 97:3 heptane:isopropanol with 0.2% dimethylethyl amine) to give two enantiomers (each >95% ee by HPLC system of separation). Take the first eluting enantiomer and treat in a similar fashion essentially as described in the previous step to give title compound as the succinate salt as a white solid.

MS (ES): m/z=327.2 [M+H], $[\alpha]_D$=+43.1° (c=0.5, MeOH).

EXAMPLES 44-47

The compounds of Examples 44-47 may be prepared essentially as described in Example 42 and Example 43. Where separation of the enantiomers is shown, this is achieved using chiral normal phase chromatography (Chiralcel OJ 4.6×250 mm column, eluting with 20:80 acetonitrile:methanol) in >95% ee.

| Ex | Compound Structure | Compound Name | MS (ES) [M + H] |
|---|---|---|---|
| 44 | 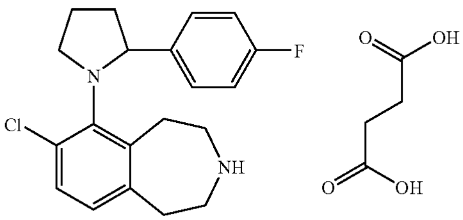 | (−)-7-Chloro-6-[2-(4-fluorophenyl)-pyrrolidin-1-yl]-2,3,4,5-tetrahydro-1H-benzo[d]azepine succinate [α]$_D$ = −41.0° (c = 0.5, MeOH) | 345.2 |
| 45 | 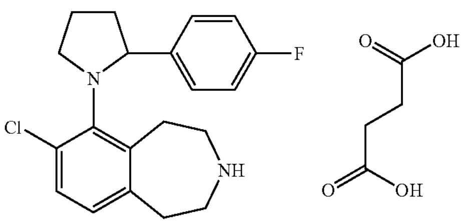 | (+)-7-Chloro-6-[2-(4-fluorophenyl)-pyrrolidin-1-yl]-2,3,4,5-tetrahydro-1H-benzo[d]azepine succinate [α]$_D$ = +43.3° (c = 0.5, MeOH) | 345.2 |
| 46 | 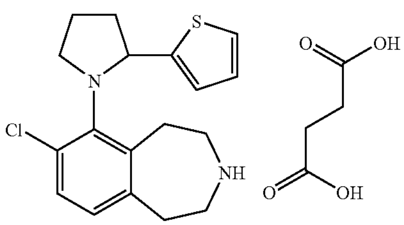 | (−)-7-Chloro-6-(2-thiophen-2-yl-pyrrolidin-1-yl)-2,3,4,5-tetrahydro-1H-benzo[d]azepine succinate [α]$_D$ = −39.2° (c = 0.5, MeOH) | 333.2 |
| 47 | 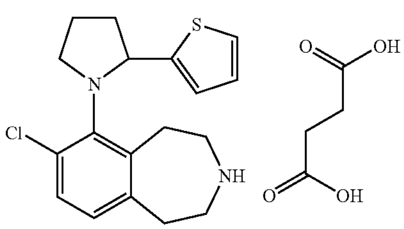 | (+)-7-Chloro-6-(2-thiophen-2-yl-pyrrolidin-1-yl)-2,3,4,5-tetrahydro-1H-benzo[d]azepine succinate [α]$_D$ = +43.1° (c = 0.5, MeOH) | 333.2 |

EXAMPLE 48

(+/−)-7-Chloro-6-(2-phenyl-pyrrolidin-1-yl)-2,3,4,5-tetrahydro-1H-benzo[d]azepine hydrochloride Treat (+/−)-7-chloro-3-(2,2,2-trifluoroacetyl)-6-(2-phenyl-pyrrolidin-1-yl)-2,3,4,5-tetrahydro-1H-benzo[d]azepine (prepared essentially as described in Preparation 38) (80 mg, 0.19 mmol) with basic methanol in a similar fashion to the isolated enantiomers of (+/−)-7-chloro-3-(2,2,2-trifluoroacetyl)-6-(2-phenyl-pyrrolidin-1-yl)-2,3,4,5-tetrahydro-1H-benzo[d]azepine. Treat the resultant residue with excess 2 N HCl in diethyl ether to give the product as a white solid (57 mg, 82%).

MS (ES): m/z=327.2 [M+H].

EXAMPLES 49 AND 50

(+ and −)-7-Chloro-6-(2-methyl-pyrrolidin-1-yl)-2,3,4,5-tetrahydro-1H-benzo[d]azepine succinate

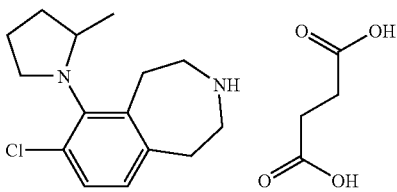

(+)-7-Chloro-6-(2-methyl-pyrrolidin-1-yl)-2,3,4,5-tetrahydro-1H-benzo[d]azepine succinate (Example 49)

Separate the enantiomers of the (+/−)-7-chloro-3-benzyloxycarbonyl-6-(2-methylpyrrolidin-1-yl)-2,3,4,5-tetrahydro-1H-benzo[d]azepine mixture via chiral normal phase chromatography (prepared essentially as described in Preparation 43) to give two enantiomers (each >95% ee by the HPLC system of separation). Take the second eluting enantiomer (350 mg, 0.88 mmol) and dissolve in 20:1 THF:concentrated HCl solution (21 mL) and add 10% palladium on activated carbon (Degussa type) (250 mg) and stir at RT under 30 psi hydrogen atmosphere for 4 h. Filter the reaction, concentrate the filtrate and purify (silica gel chromatography, eluting with 5:95 DCM:2 M ammonia in methanol) to give the product as the freebase. Dissolve the material in methanol and add succinic acid (1 equivalent) and stir until a solution results. Concentrate the reaction to a solid, triturate the solid with diethyl ether, and concentrate to a solid. Dry the solid under vacuum at 50° C. for 16 h to give the title compound (245 mg, 73%) as a white solid.

MS (ES): m/z=265.2 [M+H], $[\alpha]_D$=+48° (c=0.5, MeOH).

(−)-7-Chloro-6-(2-methyl-pyrrolidin-1-yl)-2,3,4,5-tetrahydro-1H-benzo[d]azepine succinate
(Example 50)

After separating the enantiomers of the (+/−)-7-chloro-3-benzyloxycarbonyl-6-(2-methylpyrrolidin-1-yl)-2,3,4,5-tetrahydro-1H-benzo[d]azepine mixture via chiral normal phase chromatography to give two enantiomers, take the first eluting enantiomer (70 mg) and react under similar hydrogenolysis and purification conditions followed by treatment with succinic acid (1 equivalent) to give the product as a white solid.

MS (ES): m/z=265.2 [M+H], Optical rotation (0.5% methanol)=−48.4.

The compounds of the present invention are relatively selective for the 5-HT$_{2C}$ receptor. The compounds of the present invention are particularly relatively selective for the 5-HT$_{2C}$ receptor in comparison to other 5-HT receptor subtypes and specifically the 5-HT$_{2A}$ and 5-HT$_{2B}$ receptors. This selectivity is demonstrated in the following agonist activity assays and receptor binding assays.

Agonist Activity Assays (G alpha q-GTPγ[$^{35}$S] Binding Assays)

The 5-HT$_2$ receptors are functionally coupled to specific G-proteins. Agonist activation of 5-HT$_2$ G-protein-coupled receptors results in the release of GDP from the α-subunit (G alpha q or G alpha i) of the G-protein and the subsequent binding of GTP. The binding of the stable analog GTPγ[$^{35}$S] is an indicator of receptor activation (i.e. agonist activity).

The G alpha q-GTPγ[$^{35}$S] binding assay is used to determine the in vitro potency (EC$_{50}$) and maximal efficacy (E$_{max}$, normalized to the 5-HT response) of a test compound at the 5-HT$_{2A}$, 5-HT$_{2B}$, and 5-HT$_{2C}$ receptors. The area under the dose response curve (AUC) is also determined for each receptor subtype and used to measure the test compound's selectivity for the 5-HT$_{2C}$ receptor over the 5-HT$_{2A}$ and 5-HT$_{2B}$ receptors, expressed as Selectivity Ratios (AUC 2C/2A and AUC 2C/2B, respectively). The Selectivity Ratios allow the assessment of selectivity based on both potency and efficacy. A selectivity measure that incorporates both potency and efficacy at the 5-HT$_{2C}$ receptor, as compared to the 5-HT$_{2A}$ and 5-HT$_{2B}$ receptors, is considered important due to the adverse events associated with 5-HT$_{2A}$ and 5-HT$_{2B}$ agonist activity (see introduction).

Membrane Preparation: Grow AV12 cells stably transfected with the human 5-HT$_{2A}$, 5-HT$_{2B}$, or 5-HT$_{2C}$ receptors in suspension, harvest by centrifugation, wash the cell pellet with phosphate buffered saline, pH 7.4, pellet the cells again, remove the supernatant, freeze the cell pellet on dry ice and store at −70° C. Thaw stock cell pellet and resuspend in 50 mM Tris, pH 7.4, aliquot into 1-2 mL volumes and refreeze at −70° C. for subsequent assays. (As is appreciated in the art, optimal cell quantities used per aliquot will vary with the individual transfected cell line used. In one embodiment, 5-HT$_{2A}$ and 5-HT$_{2C}$ transfected cells are typically used at about 6×10$^8$ cells per aliquot, while 5-HT$_{2B}$ cells are typically used at about 7.5×10$^8$ cells per aliquot).

On the day of assay, thaw membranes, wash the membranes with assay buffer (50 mM Tris-HCl (pH 7.4), 10 mM MgCl$_2$, 100 mM NaCl, and 0.2 mM ethylenediaminetetraacetic acid (EDTA), resuspend in assay buffer and incubate for 10 min. at 37° C. to hydrolyze any residual endogenous 5-HT. Wash the membranes again with assay buffer, and resuspend in assay buffer at a concentration to provide aliquots of about 1-4×10$^6$ cell equivalents per well (typically about 1-2×10$^6$ cell equivalents for assays with 5-HT$_{2A}$ or 5-HT$_{2C}$ receptor assays, and about 3-4×10$^6$ cell equivalents for assays with 5-HT$_{2B}$ receptor assays). Homogenize the cells with a tissue grinder and use the homogenate directly in the assay as described below.

G alpha q-GTPγ[$^{35}$S] Binding Assays: The immunoadsorption scintillation proximity assay (ISPA) of [$^{35}$S]-GTPγS binding to G alpha q is modified from published conditions (DeLapp et al, JPET 289 (1999) 946-955). Dissolve test compounds in DMSO and dilute in assay buffer to provide a range of concentrations to generate a concentration response curve. In wells of a 96 well microtiter plate, mix diluted test compound, GDP (0.1 μM final concentration), and [$^{35}$S]-GTPγS (between 0.5 and 1.0 nM final concentration). Add an aliquot of membranes to the incubation mixture and mix the plates to initiate agonist stimulation of the nucleotide exchange (200 μl final volume). Incubate the microtiter plates for 30 min. at room temperature. Quench the incubation with IGEPAL® CA-630 detergent (0.27% final concentration). Add affinity purified polyclonal rabbit anti-G alpha q antibody (about 1-2 μg per well), and anti-rabbit Ig scintillation proximity assay beads (Amersham; about 1.25 mg per well; 300 μl final volume). Seal the plates and incubate the mixture for 3 h at room temperature. Centrifuge the microtiter plates briefly to pellet beads. Quantitate the GTPγ[$^{35}$S] binding by microtiter plate scintillation spectrometry (Wallac Trilux MicroBeta™ scintillation counter).

Data Analysis: For each concentration response curve for a test compound at a given receptor, analyze the data with GraphPad Prism™ software (v3.02; GraphPad Software, San Diego, Calif.) running on a personal computer with MicroSoft Windows OS®, using nonlinear regression analysis curve fitting to determine the EC$_{50}$ and E$_{max}$ (normalized to 5-HT control curves). Determine the Area Under the agonist concentration-response Curve (AUC) with GraphPad Prism™ by the trapezoidal method.

To calculate the Selectivity Ratios, first, determine the AUC for the test compound for each receptor subtype as described above. Second, normalize the AUC's at each receptor subtype relative to the AUC determined for 5-HT at that receptor. The normalized AUC for a test compound at a given receptor is therefore expressed as a percentage of the AUC determined for 5-HT at that receptor. For example:

$5HT_{2A}$ Normalized $AUC =$ $$a = \frac{(AUC_{test\ compound}\ \text{at}\ 5HT_{2A}\ \text{receptor})}{(AUC_{5-HT}\ \text{at}\ 5HT_{2A}\ \text{receptor})} \times 100\%$$

-continued $$5HT_{2B} \text{ Normalized } AUC =$$

$$b = \frac{(AUC_{test\ compound}\ \text{at}\ 5HT_{2B}\ \text{receptor})}{(AUC_{5-HT}\ \text{at}\ 5HT_{2B}\ \text{receptor})} \times 100\%$$

$$5HT_{2C} \text{ Normalized } AUC =$$

$$c = \frac{(AUC_{test\ compound}\ \text{at}\ 5HT_{2C}\ \text{receptor})}{(AUC_{5-HT}\ \text{at}\ 5HT_{2C}\ \text{receptor})} \times 100\%$$

Third, calculate the Selectivity Ratios for the test compound as follows:

Selectivity Ratio for 5-HT$_{2C}$ receptor/5-HT$_{2A}$ receptor (AUC 2C/2A)=c/a

Selectivity Ratio for 5-HT$_{2C}$ receptor/5-HT$_{2B}$ receptor (AUC 2C/2B)=c/b

For reference purposes, the AUC 2C/2A and AUC 2C/2B for 5-HT are each 1.0. Likewise, the ratios for mCPP (meta-chlorophenylpiperazine) are tested and are found to be 2.1 and 2.1 respectively.

Representative compounds of the present invention are tested in the G alpha q-GTPγ[$^{35}$S] assays for the S-HT$_{2A}$, 5-HT$_{2B}$, and 5-HT$_{2C}$ receptors essentially as described above and are found to be a highly potent and selective agonists of the 5-HT$_{2C}$ receptor, with EC$_{50}$'s typically less than or equal to 300 nM, and AUC 2C/2A and AUC 2C/2B ratios greater than 1.5. Preferred compounds are those with EC50's less than or equal to 100 nM, and AUC 2C/2A and AUC 2C/2B ratios greater than or equal to 2.0. More preferred are those with EC50's less than or equal to 50 nM, and AUC 2C/2A and AUC 2C/2B ratios greater than or equal to 3.0.

Ligand Binding Assays

The ligand binding affinity of the compounds of the present invention to the 5-HT$_{2C}$ receptor subtype is measured essentially as described by Wainscott (Wainscott, et al., *Journal of Pharmacology and Experimental Therapeutics*, 276:720-727 (1996)). Data is analyzed by nonlinear regression analysis on the concentration response curves using the four parameter logistic equation described by DeLean (DeLean, et al, *Molecular Pharmacology*, 21, 5-16 (1982)). IC$_{50}$ values are converted to K$_i$ values using the Cheng-Prusoff equation (Cheng, et al., *Biochem. Pharmacol.*, 22, 3099-3108 (1973)).

Representative compounds of the present invention are tested essentially as described above and are found to have excellent affinity for the 5-HT$_{2C}$ receptor, with K$_i$'s typically less than or equal to about 200 nM. Preferred compounds are those with K$_i$'s of less than or equal to about 100 nM. More preferred are those with K$_i$'s less than or equal to 50 nM.

Affinities for other receptor subtypes can readily be determined by slight modification of the above described radioligand receptor binding assay using cells transfected with the desired receptor in place of cells transfected with the 5-HT$_{2C}$ receptor subtype and using an appropriate radioligand. The binding affinities for representative compounds of the present invention for a variety of receptors are determined in such assays and the compounds are found to have surprisingly higher affinity for the 5-HT$_{2C}$ receptor. Affinity for the 5-HT$_{2C}$ receptor is found to be significantly higher than for other 5-HT receptor subtypes, and notably higher than the 5-HT$_{2A}$ and 5-HT$_{2B}$ receptor subtypes. Preferred compounds are those with IC$_{50}$'s equal to or greater than 300 nM for the alpha 1 and alpha 2 adrenergic receptors and equal to or greater than 500 nM for D$_1$ and D$_2$ dopaminergic receptors. More preferred compounds are those with IC$_{50}$'s equal to or greater than 1000 mM for the alpha 1 and alpha 2 adrenergic receptors and the D$_1$ and D$_2$ dopaminergic receptors. Still more preferred are those compounds with IC$_{50}$'s equal to or greater than 3000 nM for the alpha 1 and alpha 2 adrenergic receptors and the D$_1$ and D$_2$ dopaminergic receptors.

For the above in vitro assays, exemplified compounds are assayed and found to have either an EC$_{50}$ or a K$_i$ value of equal to or less than 50 nM, and to generally have AUC 2C/2A and AUC 2C/2B ratios of greater than or equal to 2.0. Exemplified compounds are assayed and found to have alpha 1 and alpha 2 adrenergic receptor IC$_{50}$'s generally equal to or greater than 300 nM, and D$_1$ and D$_2$ dopaminergic receptor IC$_{50}$'s generally equal to or greater than 500 nM.

Rat Feeding Assays

The ability of the compounds of the present invention to treat obesity is demonstrated by testing in acute and chronic rat feeding assays.

Animals: Obtain male Long-Evans rats (Harlan Sprague-Dawley, Indianapolis, Ind.) that are approximately one hundred-days old and have been maintained on a calorie rich diet since weaning (TD 95217, 40% calories from fat; Teklad, Madison, Wis.). House the rats individually with a 12 h:12 h light:dark cycle (lights on from about 22:00 h to about 10:00 h) and maintain rats on the same diet (TD 95217) with free access to water, for about 1-2 weeks to acclimate the rats to the environment. Dose rats orally with vehicle (10% acacia with 0.15% saccharin in water) once daily for at least 1 day (typically 1-2 days) to acclimate the rats to the procedures. Randomize the rats into groups so each group has similar mean body weights.

Calorimetric Acute Feeding Assay: At approximately 8:00 h on the day of assay, weigh each rat and transfer to individual chambers of an open circuit calorimetry system (Oxymax, Columbus Instruments International Corporation; Columbus, Ohio), with free access to food (pre-weighed) and water, and begin measuring VO$_2$ and VCO$_2$. At approximately 10:00 h, dose rats orally with vehicle or test compound, return them to their calorimetry chambers, and continue measuring VO$_2$ and VCO$_2$ at regular time intervals (approximately hourly). At approximately 8:00 h the following day, measure rat body weight and the remaining food, assuming the difference in weight of food is equal to the mass of food consumed. Calculate the 24 h energy expenditure (EE) and respiratory quotient (RQ) essentially as described in Chen, Y. and Heiman, M. L., Regulatory Peptide, 92:113-119 (2000). EE during light photoperiod is indicative of the resting metabolic rate and RQ is indicative of the fuel source the animal utilizes (pure carbohydrate metabolism gives an RQ of about 1.0, pure fat metabolism gives an RQ of about 0.7, mixed carbohydrate and fat metabolism gives intermediate values for RQ). Calculate EE as the product of calorific value (CV) and VO$_2$ per body weight (kg); where CV=3.815+1.232*RQ, and RQ is the ratio of CO$_2$ produced (VCO$_2$) to O$_2$ consumed (VO$_2$). Caloric intake is calculated as (mass of 24 h food intake in grams)×(physiological fuel value of the diet in kilocalorie/g) per kg of body weight.

Acute Feeding Assay with a selective 5-HT$_{2C}$ receptor antagonist: The above calorimetric acute feeding assay is conducted with the following modifications. Open circuit calorimetry systems are not used and only the 24 h periodic food intake and body weight are measured. Three groups of rats are used with the first group receiving a subcutaneous dose of saline (0.5 mL) about 15 minutes prior to the oral dose of vehicle, the second group receiving a subcutaneous dose of saline (0.5 mL) about 15 minutes prior to the oral dose of test compound in vehicle, and the third group receiving a subcutaneous injection of a selective 5-HT$_{2C}$ receptor antagonist, 6-chloro-5-methyl-N-{2-[(2-methylpyridin-3-yl-oxy)pyridin-5-yl]aminocarbonyl}-2,3-dihydroindole (3 mg/Kg, in 35% cyclodextrin, 0.5 mL), about 15 min. prior to the oral dose of test compound in vehicle.

Chronic Feeding Assay: At between approximately 8:00 h and 10:00 h on day one of the assay, weigh and orally dose each rat with vehicle or test compound and return the animal to its home cage, with free access to food (pre-weighed) and water. For each of days 2-15, at between approximately 8:00 h and 10:00 h, measure rat body weight and the weight of food consumed in the last 24 h period, and administer daily oral dose of test compound or vehicle. On days −2 and 15 measure total fat mass and lean mass by nuclear magnetic resonance (NMR) using an EchoMRI™ system (Echo Medical Systems, Houston Tex.). (See Frank C. Tinsley, Gersh Z. Taicher, and Mark L. Heiman, "Evaluation of a New Quantitative Magnetic Resonance (QMR) Method for Mouse Whole Body Composition Analysis", Obesity Research, submitted May 1, 2003.)

Representative compounds of the present invention are tested in acute and chronic feeding assays essentially as described above. In the acute assays, the compounds are found to significantly reduce 24 h food intake, which effect is blocked by pre-administration of the 5-$HT_{2C}$ receptor antagonist. The compounds also are found to dose-dependently reduce RQ without significantly changing the energy expenditure during the light photo-period. Thus the compounds are found to reduce caloric intake and increase the proportion of fuel deriving from fat utilization, without significantly changing the resting metabolic rate. In the chronic assay, the compounds are found to significantly decrease cumulative food intake and cumulative body weight change in a dose-dependent manner compared to control animals. The decrease in body weight is found to be due to loss of adipose tissue while lean body mass is not changed.

The ability of the 5-$HT_{2C}$ receptor agonists of the present invention to treat obsessive/compulsive disorder is demonstrated by testing in a variety of in vivo assays as follows:

Marble Burying Assay

Marble burying in mice has been used to model anxiety disorders including obsessive-compulsive disorders (OCD) due to ethological study of the behavior (e.g. Gyertyan I. "Analysis of the marble burying response: Marbles serve to measure digging rather than evoke burying", *Behavioural Pharmacology* 6: 24-31, (1995)) and due to the pharmacological effects of clinical standards (c.f., Njung'E K. Handley S L. "Evaluation of marble-burying behavior as a model of anxiety", *Pharmacology, Biochemistry & Behavior.* 38: 63-67, (1991)); Borsini F., Podhoma J., and Marazziti, D. "Do animal models of anxiety predict anxiolytic effects of antidepressants?", *Psychopharmacology* 163: 121-141, (2002)). Thus, drugs used in the treatment of generalized anxiety in humans (e.g. benzodiazepines) as well as compounds used to treat OCD (e.g. SSRIs like fluoxetine) decrease burying.

House experimentally-naïve male, NIH Swiss mice (Harlan Sprague-Dawley, Indianapolis, Ind.) weighing between 28-35 g in groups of 12 for at least three days prior to testing in a vivarium with 12 h light and dark cycles. Conduct experiments during the light cycle in a dimly lit experimental testing room. Dose mice with vehicle or test compound and, after a specified pretreatment interval (generally 30 min.), place each mouse individually on a rotorod (Ugo Basile 7650) operating at a speed of 6 revolutions/min. and observe for falling. After 2 min. on the rotorod, place the mice individually in a 17×28×12 cm high plastic tub with 5 mm sawdust shavings on the floor that are covered with 20 blue marbles (1.5 cm diameter) placed in the center. After 30 min., count the number of marbles buried (⅔ covered with sawdust). Assess the test compound's effect on marble burying with Dunnett's test and the effect on rotorod performance by Fisher's exact test.

Clinically effective standard compounds suppress marble burying at doses that are devoid of motor-impairing effects as measured on the rotorod. The in vivo efficacy of 5$HT_{2C}$ compounds at the 5$HT_{2C}$ receptor is confirmed by the prevention of effects of the 5$HT_{2C}$ agonists on marble burying by co-administration of the 5$HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the marble burying assay essentially as described and are surprisingly found to reduce burying behavior in the test mice. The reduction of burying behavior is found to be blocked by co-administration of the 5-$HT_{2C}$ antagonist. In contrast to the compounds of the present invention, the anxiolytic compound chlordiazepoxide and the antipsychotic compound chlorpromazine decrease marble burying only at doses that also disrupt rotorod performance.

Nestlet Shredding

Mice naturally will construct nests of material available in their living environment. Since this behavior is obsessive in nature, it has been used to model OCD (Xia Li, Denise Morrow and Jeffrey M. Witkin, "Decreases in nestlet shredding of mice by serotonin uptake inhibitors: comparison with marble burying", Psychopharmacology, submitted Jul. 14, 2003). House experimentally-naïve male, NIH Swiss mice (Harlan Sprague-Dawley, Indianapolis, Ind.) weighing between 28-35 g in groups of 12 for at least three days prior to testing in a vivarium with a 12 h light/dark cycle. Conduct experiments during the light cycle in an experimental room with normal overhead fluorescent lighting. Dose mice with vehicle or test compound and after a specified pretreatment interval (generally 30 min.), place the mice individually in a 17×28×12 cm high plastic tub with about 5 mm sawdust shavings on the floor along with a pre-weighed multi-ply gauze pad (51 mm square). After 30 min., weigh the remainder of the gauze pad not removed by the mouse. Determine the weight of the gauze used for nestlet construction by subtraction. Compare the results for test compound treated mice to the results for vehicle control treated mice with Dunnett's test.

Clinically effective OCD treatment standard compounds suppress nestlet shredding at doses that are devoid of motor-impairing effects as measured by the rotorod test. The in vivo efficacy of 5$HT_{2C}$ compounds at the 5$HT_{2C}$ receptor is confirmed by the prevention of effects of the 5$HT_{2C}$ agonists on nestlet shredding by co-administration of the 5$HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed essentially as described above and are surprisingly found to suppress nestlet shredding at doses that are devoid of motor-impairing effects as measured by the rotorod test.

In contrast to the compounds of the present invention, the anxiolytic chlordiazepoxide and the psychomotor stimulant d-amphetamine decreases nestlet shredding only at doses that produce motoric side effects (depression or stimulation, respectively).

Schedule-Induced Polydipsia

Food-deprived rats exposed to intermittent presentations of food will drink amounts of water that are far in excess of their normal daily intake and in excess of their intake when given all of their food at one time (Falk J L. "Production of polydipsia in normal rats by an intermittent food schedule", *Science* 133: 195-196, (1961)). This excessive behavior is persistent and has been used to model OCD.

Maintain Wistar rats on a food restricted diet (to maintain 85% free feeding weight), but with free access to water. Train the rats in a behavioral testing chamber to press a lever to receive a food pellet under a fixed interval schedule, such that the rats are rewarded with a 45 mg food pellet the first time they press a lever after a 120 second interval has elapsed. The fixed interval is then reset to 120 seconds and the process repeated. Thus, during a 90 min. test session, the rats can earn a maximum of 45 pellets. The behavioral chamber is also equipped with a water bottle that is weighed before and after the session to determine the amount of water consumed.

Administer test compounds on Tuesdays and Fridays. Determine control day performances on Thursdays. Administer compounds either orally at 60 min. before the beginning of a test session, or subcutaneously at 20 min. before the beginning of a test session. Compare the rates of lever pressing and water consumption for each animal's performance during sessions after test compound treatment with that animal's performance during control sessions, expressed as a percent of the control rate. Average the individual percent of control rates for each dose and calculate the standard error of the mean.

Clinically effective OCD treatment standard compounds (e.g. chlomipramine, fluoxetine) suppress schedule-induced polydipsia without producing notable changes in motor patterns, food intake, or behavior the following day. The in vivo efficacy of $5HT_{2C}$ compounds at the $5HT_{2C}$ receptor is confirmed by the prevention of effects of the $5HT_{2C}$ agonists on excessive drinking by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the schedule-induced polydipsia assay essentially as described above and are surprisingly found to suppress schedule-induced polydipsia without producing notable changes in motor patterns, food intake, or behavior the following day. The behavior suppression is blocked by co-administration of the $5-HT_{2C}$ antagonist.

In contrast to the compounds of the present invention, the psychomotor stimulant d-amphetamine decreases excessive drinking only at behaviorally stimulating doses and these effects are not prevented by the $5HT_{2C}$ receptor antagonist.

While it is possible to administer compounds employed in the methods of this invention directly without any formulation, the compounds are usually administered in the form of pharmaceutical compositions comprising a pharmaceutically acceptable excipient and at least one compound of Formula I or a pharmaceutically acceptable salt thereof. These compositions can be administered by a variety of routes including oral, rectal, transdermal, subcutaneous, intravenous, intramuscular, and intranasal. The compounds employed in the methods of this invention are effective as both injectable and oral compositions. Such compositions are prepared in a manner well known in the pharmaceutical art. See, e.g. REMINGTON'S PHARMACEUTICAL SCIENCES, (16th ed. 1980).

In making the compositions employed in the present invention the active ingredient is usually mixed with at least one excipient, diluted by at least one excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Under some circumstances, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compound employed, the type of pharmacokinetic profile desired from the route of administration, and the state of the patient.

We claim:
1. A compound of Formula I:

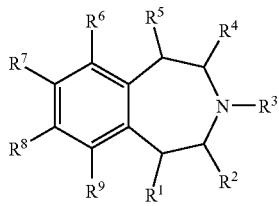

where:
$R^1$ is hydrogen;
$R^2$, $R^3$, and $R^4$ are each hydrogen;
$R^5$ is hydrogen;
$R^6$ is selected from the group consisting of

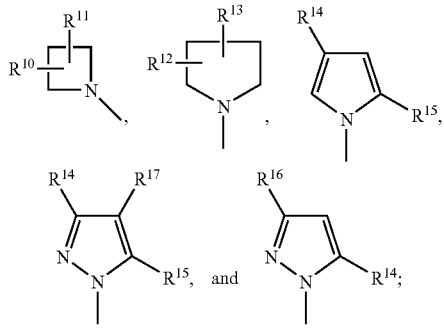

$R^7$ is chloro;
$R^8$ is hydrogen;
$R^9$ is hydrogen;

$R^{10}$ is hydrogen, 3-hydroxy, $(C_1$-$C_5)$alkyl optionally substituted with 1-6 fluoro groups, $Ph^1$-$(C_0$-$C_3)$alkyl, or $Ar^1$—$(C_0$-$C_3)$alkyl;
$R^{11}$ is hydrogen or $(C_1$-$C_3)$alkyl optionally substituted with 1-5 fluoro groups;
$R^{12}$ is hydrogen, $(C_1$-$C_5)$alkyl optionally substituted with 1-6 fluoro groups, $Ph^1$-$(C_0$-$C_3)$alkyl, or $Ar^1$—$(C_0$-$C_3)$alkyl;
$R^{13}$ is hydrogen or $(C_1$-$C_3)$alkyl optionally substituted with 1-5 fluoro groups;
$R^{14}$ is hydrogen, methyl or —$CF_3$;
$R^{15}$ is $(C_1$-$C_5)$alkyl, —$CF_3$, $Ph^1$, or $Ar^2$;
$R^{16}$ is $Ph^1$-$(C_1$-$C_3)$alkyl or $Ph^1$-$S$—$CH_2$—;
$R^{17}$ is hydrogen, halo, or methyl, provided that $R^{17}$ is hydrogen when $R^{15}$ is $Ph^1$ or $Ar^2$;
$Ph^1$ is phenyl optionally substituted with
  a) 1 to 5 fluoro substituents;
  b) 1 to 3 substituents independently selected from the group consisting of halo, cyano, methyl, hydroxy, and methoxy; or
  c) —$CF_3$ and optionally further substituted with 1 or 2 fluoro substituents;
$Ar^1$ is thienyl or pyridyl optionally substituted with
  a) 1 to 3 fluoro substituents; or
  b) 1 to 2 substituents independently selected from the group consisting of halo, cyano, and methyl;
$Ar^2$ is furyl, thienyl, or pyridyl optionally substituted with 1 to 2 substituents independently selected from the group consisting of halo, cyano, and methyl;
or a pharmaceutically acceptable salt thereof.

2. A pharmaceutical composition comprising a compound according to claim 1, or a pharmaceutically acceptable salt thereof, as an active ingredient in association with a pharmaceutically acceptable carrier, diluent or excipient.

3. A method for the treatment of obesity in mammals, comprising administering to a mammal in need of such treatment an effective amount of a compound according to claim 1, or a pharmaceutically acceptable salt thereof.

4. The method of claim 3, where the mammal is human.

5. A method for the treatment of obsessive compulsive disorder in mammals, comprising administering to a mammal in need of such treatment an effective amount of a compound according to claim 1, or a pharmaceutically acceptable salt thereof.

6. The method of claim 5, where the mammal is human.

7. A method for the treatment of anxiety in mammals, comprising administering to a mammal in need of such treatment an effective amount of a compound according to claim 1, or a pharmaceutically acceptable salt thereof.

8. The method of claim 7, where the mammal is human.

* * * * *